US011075000B2

United States Patent
Mason et al.

(10) Patent No.: US 11,075,000 B2
(45) Date of Patent: Jul. 27, 2021

(54) METHOD AND SYSTEM FOR USING VIRTUAL AVATARS ASSOCIATED WITH MEDICAL PROFESSIONALS DURING EXERCISE SESSIONS

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 0 days.

(21) Appl. No.: 17/147,211

(22) Filed: Jan. 12, 2021

(65) Prior Publication Data
US 2021/0134426 A1 May 6, 2021

Related U.S. Application Data

(63) Continuation-in-part of application No. 17/021,895, filed on Sep. 15, 2020.
(Continued)

(51) Int. Cl.
*G16H 80/00* (2018.01)
*G16H 20/30* (2018.01)
(Continued)

(52) U.S. Cl.
CPC ............. *G16H 20/30* (2018.01); *G06F 3/011* (2013.01); *G06F 3/016* (2013.01); *G06N 20/00* (2019.01); *G16H 80/00* (2018.01)

(58) Field of Classification Search
CPC ........ G16H 20/30; G16H 80/00; G06N 20/00; G16F 3/011; G16F 3/016
See application file for complete search history.

(56) References Cited

U.S. PATENT DOCUMENTS 6,182,029 B1 1/2001 Friedman
6,413,190 B1 7/2002 Wood et al.
(Continued)

FOREIGN PATENT DOCUMENTS

| CA | 2698078 A1 | 3/2010 |
|---|---|---|
| CN | 112603295 A | 2/2003 |
| WO | 2019204876 A1 | 4/2019 |

*Primary Examiner* — George Manuel
(74) *Attorney, Agent, or Firm* — Dickinson Wright, PLLC; Stephen A. Mason; Jonathan H. Harder

(57) ABSTRACT

A computer-implemented system includes a treatment apparatus manipulated by a patient while performing an exercise session and a patient interface that receives a virtual avatar. The patient interface presents the virtual avatar. The virtual avatar uses a virtual representation of the treatment apparatus to guide the patient through an exercise session. A server computing device provides the virtual avatar of the patient to the patient interface and receives a message pertaining to a trigger event. The message includes a severity level of the trigger event. The server computing device determines whether a severity level of the trigger event exceeds a threshold severity level, and responsive to determining the severity level of the trigger event exceeds the threshold severity level, replaces on the patient interface the presentation of the virtual avatar with a presentation of a multimedia feed from a computing device of the medical professional.

30 Claims, 12 Drawing Sheets

Related U.S. Application Data

(60) Provisional application No. 62/910,232, filed on Oct. 3, 2019, provisional application No. 63/104,716, filed on Oct. 23, 2020.

(51) Int. Cl.
    *G06F 3/01*     (2006.01)
    *G06N 20/00*     (2019.01)

(56) References Cited

U.S. PATENT DOCUMENTS

| | | |
|---|---|---|
| 6,491,649 B1 | 12/2002 | Ombrellaro |
| 7,169,085 B1 | 1/2007 | Killin et al. |
| 7,209,886 B2 | 4/2007 | Kimmel |
| 7,974,689 B2 | 7/2011 | Volpe et al. |
| 8,751,264 B2 | 6/2014 | Beraja et al. |
| 8,823,448 B1 | 9/2014 | Shen |
| 9,311,789 B1 | 4/2016 | Gwin |
| 9,939,784 B1 | 4/2018 | Berardinelli |
| 10,130,298 B2 | 11/2018 | Mokaya et al. |
| 10,424,033 B2 | 9/2019 | Romeo |
| 2003/0036683 A1 | 2/2003 | Kehr et al. |
| 2006/0064329 A1 | 3/2006 | Abolfathi et al. |
| 2009/0011907 A1 | 1/2009 | Radow et al. |
| 2009/0070138 A1 | 3/2009 | Langheier et al. |
| 2010/0268304 A1 | 10/2010 | Matos |
| 2011/0172059 A1 | 7/2011 | Watterson et al. |
| 2011/0218814 A1 | 9/2011 | Coats |
| 2012/0065987 A1 | 3/2012 | Farooq et al. |
| 2012/0190502 A1 | 7/2012 | Paulus et al. |
| 2012/0310667 A1 | 12/2012 | Altman et al. |
| 2013/0123667 A1 | 5/2013 | Komatireddy et al. |
| 2013/0296987 A1 | 11/2013 | Rogers et al. |
| 2014/0006042 A1 | 1/2014 | Keefe et al. |
| 2014/0188009 A1 | 7/2014 | Lange et al. |
| 2014/0194250 A1 | 7/2014 | Reich et al. |
| 2014/0257837 A1* | 9/2014 | Walker .................. G16H 50/30 705/2 |
| 2014/0322686 A1 | 10/2014 | Kang |
| 2015/0088544 A1 | 3/2015 | Goldberg |
| 2015/0161331 A1 | 6/2015 | Oleynik |
| 2015/0339442 A1 | 11/2015 | Oleynik |
| 2016/0140319 A1 | 5/2016 | Stark et al. |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2017/0004260 A1 | 1/2017 | Moturu et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0243028 A1 | 8/2017 | LaFever et al. |
| 2017/0278209 A1 | 9/2017 | Olsen et al. |
| 2017/0300654 A1 | 10/2017 | Stein et al. |
| 2017/0329917 A1 | 11/2017 | McRaith et al. |
| 2017/0344726 A1 | 11/2017 | Duffy et al. |
| 2017/0360586 A1 | 12/2017 | Dempers et al. |
| 2018/0052962 A1 | 2/2018 | Van Der Koijk et al. |
| 2018/0085615 A1 | 3/2018 | Astolfi et al. |
| 2018/0102190 A1 | 4/2018 | Hogue et al. |
| 2018/0240552 A1 | 8/2018 | Tuyl et al. |
| 2018/0271432 A1 | 9/2018 | Auchinleck et al. |
| 2018/0280784 A1 | 10/2018 | Romeo et al. |
| 2018/0330824 A1 | 11/2018 | Athey et al. |
| 2019/0019578 A1 | 1/2019 | Vaccaro |
| 2019/0066832 A1 | 2/2019 | Kang et al. |
| 2019/0167988 A1 | 6/2019 | Shahriari et al. |
| 2020/0143922 A1 | 5/2020 | Chekroud et al. |
| 2020/0151595 A1 | 5/2020 | Jayalath et al. |
| 2020/0152339 A1 | 5/2020 | Pulitzer et al. |
| 2020/0160198 A1 | 5/2020 | Reeves et al. |
| 2020/0176098 A1 | 6/2020 | Lucas et al. |
| 2020/0293712 A1 | 9/2020 | Potts et al. |
| 2020/0401224 A1 | 12/2020 | Cotton |

\* cited by examiner

METHOD AND SYSTEM FOR USING VIRTUAL AVATARS ASSOCIATED WITH MEDICAL PROFESSIONALS DURING EXERCISE SESSIONS

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. This application also claims priority to and the benefit of U.S. Provisional Patent Application Ser. No. 63/104,716, filed Oct. 23, 2020, titled "Method and System for Using Virtual Avatars Associated with Medical Professionals During Exercise Sessions," the entire disclosure of which is hereby incorporated by reference for all purposes.

BACKGROUND

Remote medical assistance, or telemedicine, may aid a patient in performing various aspects of a rehabilitation regimen for a body part. The patient may use a patient interface in communication with an assistant interface for receiving the remote medical assistance via audio and/or audiovisual communications.

SUMMARY

In one embodiment, a computer-implemented system includes a treatment apparatus manipulated by a patient while performing an exercise session and a patient interface that receives a virtual avatar. The patient interface presents the virtual avatar. The virtual avatar uses a virtual representation of the treatment apparatus to guide the patient through an exercise session. A server computing device provides the virtual avatar of the patient to the patient interface and receives a message pertaining to a trigger event. The message includes a severity level of the trigger event. The server computing device determines whether a severity level of the trigger event exceeds a threshold severity level, and responsive to determining the severity level of the trigger event exceeds the threshold severity level, replaces on the patient interface the presentation of the virtual avatar with a presentation of a multimedia feed from a computing device of the medical professional.

In one embodiment, a method includes operations performed by one or more processing devices described herein.

In one embodiment, a system includes a memory that stores instructions and a processing device communicatively coupled to the memory. The processing device executes the instructions to perform any of the methods, operations, or steps described herein.

In one embodiment, a tangible, non-transitory computer-readable medium stores instructions that, when executed, cause a processing device to perform any of the methods, operations, or steps described herein.

BRIEF DESCRIPTION OF THE DRAWINGS

For a detailed description of example embodiments, reference will now be made to the accompanying drawings in which.

NOTATION AND NOMENCLATURE

Figure 1:
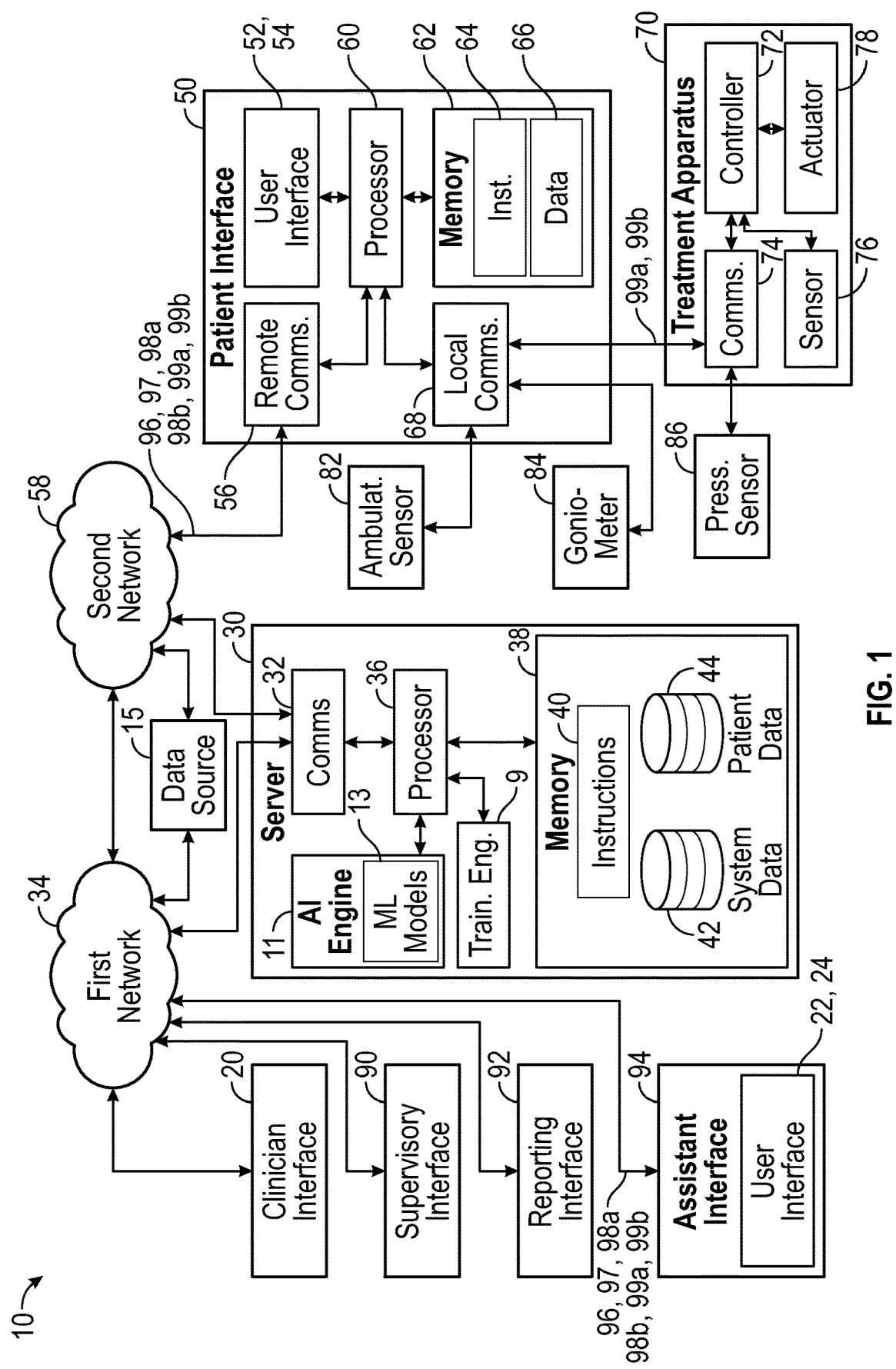
FIG. 1 shows a block diagram of an embodiment of a computer implemented system for managing a treatment plan according to the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, etc. may be used interchangeably herein.

The term "optimal treatment plan" may refer to optimizing a treatment plan based on a certain parameter or combinations of more than one parameter, such as, but not limited to, a monetary value amount generated by a treatment plan and/or billing sequence, wherein the monetary value amount is measured by an absolute amount in dollars or another currency, a Net Present Value (NPV) or any other measure, a patient outcome that results from the treatment plan and/or billing sequence, a fee paid to a medical professional, a payment plan for the patient to pay off an amount of money owed or a portion thereof, a plan of reimbursement, an amount of revenue, profit or other monetary value amount to be paid to an insurance or third-party provider, or some combination thereof.

Real-time may refer to less than or equal to 2 seconds. Near real-time may refer to any interaction of a sufficiently short time to enable two individuals to engage in a dialogue via such user interface, and will generally be less than 10 seconds but greater than 2 seconds.

Any of the systems and methods described in this disclosure may be used in connection with rehabilitation. Rehabilitation may be directed at cardiac rehabilitation, rehabilitation from stroke, multiple sclerosis, Parkinson's disease, myasthenia gravis, Alzheimer's disease, any other neurodegenerative or neuromuscular disease, a brain injury, a spinal cord injury, a spinal cord disease, a joint injury, a joint disease, or the like. Rehabilitation can further involve muscular contraction in order to improve blood flow and lymphatic flow, engage the brain and nervous system to control and affect a traumatized area to increase the speed of healing, reverse or reduce pain (including arthralgias and myalgias), reverse or reduce stiffness, recover range of motion, encourage cardiovascular engagement to stimulate the release of pain-blocking hormones or to encourage highly oxygenated blood flow to aid in an overall feeling of well-being. Rehabilitation may be provided for individuals of average height in reasonably good physical condition having no substantial deformities, as well as for individuals more typically in need of rehabilitation, such as those who are elderly, obese, subject to disease processes, injured and/or who have a severely limited range of motion. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through, dissecting and/or harming numerous muscles and muscle groups in or about, without limitation, the skull or face, the abdomen, the ribs and/or the thoracic cavity, as well as in or about all joints and appendages. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. Performance of the one or more sets of exercises may be required in order to qualify for an elective surgery, such as a knee replacement. The patient may prepare an area of his or her body for the surgical procedure by performing the one or more sets of exercises, thereby strengthening muscle groups, improving existing muscle memory, reducing pain, reducing stiffness, establishing new muscle memory, enhancing mobility (i.e., improve range of motion), improving blood flow, and/or the like.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain characteristics (e.g., vital-sign or other measurements; performance; demographic; geographic; diagnostic; measurement- or test-based; medically historic; etiologic; cohort-associative; differentially diagnostic; surgical, physically therapeutic, pharmacologic and other treatment(s) recommended; arterial blood gas and/or oxygenation levels or percentages; psychographics; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, or some combination thereof. The measurement information may include, e.g., a vital sign, a respiration rate, a heartrate, a temperature, a blood pressure, arterial blood gas and/or oxygenation levels or percentages, glucose levels or levels of other biomarkers, or some combination thereof. It may be desirable to process the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, a treatment apparatus used by the patient at the location at which the patient is located. Oftentimes, when a patient undergoes rehabilitative surgery (e.g., knee surgery), a physical therapist or other medical professional may prescribe a treatment apparatus to the patient to use to perform a treatment protocol at their residence or any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

Since the physical therapist or other medical professional is located in a different location from the patient and the treatment apparatus, it may be technically challenging for the physical therapist or other medical professional to monitor the patient's actual progress (as opposed to relying on the patient's word about their progress) using the treatment apparatus, modify the treatment plan according to the patient's progress, adapt the treatment apparatus to the personal characteristics of the patient as the patient performs the treatment plan, and the like.

Accordingly, some embodiments of the present disclosure pertain to using artificial intelligence and/or machine learning to dynamically control a treatment apparatus based on the assignment during an adaptive telemedical session. In some embodiments, numerous treatment apparatuses may be provided to patients. The treatment apparatuses may be used by the patients to perform treatment plans in their residences, at a gym, at a rehabilitative center, at a hospital, at a work site, or any suitable location, including permanent or temporary domiciles. In some embodiments, the treatment apparatuses may be communicatively coupled to a server. Characteristics of the patients may be collected before, during, and/or after the patients perform the treatment plans. For example, the personal information, the performance information, and the measurement information may be collected before, during, and/or after the person performs the treatment plans. The results (e.g., improved performance or decreased performance) of performing each exercise may be collected from the treatment apparatus throughout the treatment plan and after the treatment plan is performed. The parameters, settings, configurations, etc. (e.g., position of pedal, amount of resistance, etc.) of the treatment apparatus may be collected before, during, and/or after the treatment plan is performed.

Each characteristic of the patient, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment apparatuses and/or any suitable computing device (e.g., computing devices where personal information is entered, such as a clinician interface or patient interface) over time as the patients use the treatment apparatuses to perform the various treatment plans. The data that may be collected may include the characteristics of the patients, the treatment plans performed by the patients, and the results of the treatment plans.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment apparatus for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment apparatus while the new patient uses the treatment apparatus to perform the treatment plan.

As may be appreciated, the characteristics of the new patient may change as the new patient uses the treatment apparatus to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion. A different treatment plan may be selected for the new patient, and the treatment apparatus may be controlled, distally and based on the different treatment plan, the treatment apparatus while the new patient uses the treatment apparatus to perform the treatment plan. Such techniques may provide the technical solution of distally controlling a treatment apparatus. Further, the techniques may lead to faster recovery times and/or better results for the patients because the treatment plan that most accurately fits their characteristics is selected and implemented, in real-time, at any given moment. Real-time may refer to less than or equal to 2 seconds. Near real-time may refer to any interaction of a sufficiently short time to enable two individuals to engage in a dialogue via such user interface, and will generally be less than 10 seconds but greater than 2 seconds. As described herein, the term "results" may refer to medical results or medical outcomes. Results and outcomes may refer to responses to medical actions.

In some embodiments, the treatment plans may be presented, during a telemedicine or telehealth session, to a medical professional. The medical professional may select a particular treatment plan for the patient to cause that treatment plan to be transmitted to the patient and/or to control, based on the treatment plan, the treatment apparatus. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment apparatus. In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text and other multimedia information.

Presenting the treatment plans generated by the artificial intelligence engine concurrently with a presentation of the patient video may provide an enhanced user interface because the medical professional may continue to visually and/or otherwise communicate with the patient while also reviewing the treatment plans on the same user interface. The enhanced user interface may improve the medical professional's experience using the computing device and may encourage the medical professional to reuse the user interface. Such a technique may also reduce computing resources (e.g., processing, memory, network) because the medical professional does not have to switch to another user interface screen to enter a query for a treatment plan to recommend based on the characteristics of the patient. The artificial intelligence engine provides, dynamically on the fly, the treatment plans and excluded treatment plans.

In some embodiments, the treatment plan may be modified by a medical professional. For example, certain procedures may be added, modified or removed. In the telehealth scenario, there are certain procedures that may not be performed due to the distal nature of a medical professional using a computing device in a different physical location than a patient.

A potential technical problem may relate to the information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). That is, some sources used by various medical professional entities may be installed on their local computing devices and, additionally and/or alternatively, may use proprietary formats. Accordingly, some embodiments of the present disclosure may use an API to obtain, via interfaces exposed by APIs used by the sources, the formats used by the sources. In some embodiments, when information is received from the sources, the API may map and convert the format used by the sources to a standardized (i.e., canonical) format, language and/or encoding ("format" as used herein will be inclusive of all of these terms) used by the artificial intelligence engine. Further, the information converted to the standardized format used by the artificial intelligence engine may be stored in a database accessed by the artificial intelligence engine when the artificial intelligence engine is performing any of the techniques disclosed herein. Using the information converted to a standardized format may enable a more accurate determination of the procedures to perform for the patient and/or a billing sequence to use for the patient.

The various embodiments disclosed herein may provide a technical solution to the technical problem pertaining to the patient's medical condition information being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). The information may be converted from the format used by the sources to the standardized format used by the artificial intelligence engine. Further, the information converted to the standardized format used by the artificial intelligence engine may be stored in a database accessed by the artificial intelligence engine when performing any of the techniques disclosed herein. The standardized information may enable generating optimal treatment plans, where the generating is based on treatment plans associated with the standardized information, monetary value amounts, and the set of constraints. The optimal treatment plans may be provided in a standardized format that can be processed by various applications (e.g., telehealth) executing on various computing devices of medical professionals and/or patients.

A technical problem may include the challenge of enabling one medical professional to treat numerous patients at the same time. A technical solution to the technical problem may include the enablement of at least one medical professional or a group of medical professionals, wherein one medical professional may participate at one time and a different medical professional may participate at another time, to treat numerous patients at the same time. As used herein the term "a single medical professional" (or "one medical professional" or equivalent) shall be deemed inclusive of all of the scenarios just recited. For example, in group therapy or recovery sessions, it may be desirable for a single medical professional to view, monitor, treat, manage, diagnose, etc. more than one patient at the same time from a distal location. Accordingly, in some embodiments of the present disclosure, a virtual avatar is used to guide each patient through an exercise session of a treatment plan. The medical professional may use a computing device to view, monitor, treat, manage, diagnose, etc. the patients at once or in temporally close ranges. If a trigger event occurs, such as a user indicating they are in a substantial amount of pain, a telemedicine session is initiated either by selection or electronically. The telemedicine session causes the virtual avatar to be replaced on the computing device of the patient with a multimedia feed from the computing device of the medical professional. In some embodiments, the medical professional may select to intervene and/or interrupt any patient's treatment plan (including, for example and without limitation, an exercise, rehabilitation, prehabilitation, or other session) as desired (e.g., when the medical professional determines a sensor measurement is undesired, the patient is not performing as desired, etc.), while the other patients continue to follow the virtual avatar to perform the exercise session.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a medical professional may adapt, remotely during a telemedicine session, the treatment apparatus to the needs of the patient by causing a control instruction to be transmitted from a server to treatment apparatus. Such adaptive nature may improve the results of recovery for a patient, furthering the goals of personalized medicine, and enabling personalization of the treatment plan on a per-individual basis.

FIG. 1 shows a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients.

The system data store 42 may be configured to hold data relating to billing procedures, including rules and constraints pertaining to billing codes, order, timing, insurance regimes, laws, regulations, or some combination thereof. The system data store 42 may be configured to store various billing sequences generated based on billing procedures and various parameters (e.g., monetary value amount generated, patient outcome, plan of reimbursement, fees, a payment plan for patients to pay of an amount of money owed, an amount of revenue to be paid to an insurance provider, etc.). The system data store 42 may be configured to store optimal treatment plans generated based on various treatment plans for users having similar medical conditions, monetary value amounts generated by the treatment plans, and the constraints. Any of the data stored in the system data store 42 may be accessed by an artificial intelligence engine 11 when performing any of the techniques described herein.

The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

In addition, the characteristics (e.g., personal, performance, measurement, etc.) of the people, the treatment plans followed by the people, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment apparatuses and/or computing devices over time and stored in the patient data store. The characteristic data, treatment plan data, and results data may be correlated in the patient-cohort databases in the patient data store 44. The characteristics of the people may include personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute the artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control a treatment apparatus 70, among other things. The machine learning models 13 may be trained to generate, based on billing procedures, billing sequences and/or treatment plans tailored for various parameters (e.g., a fee to be paid to a medical professional, a payment plan for the patient to pay off an amount of money owed, a plan of reimbursement, an amount of revenue to be paid to an insurance provider, or some combination thereof). The machine learning models 13 may be trained to generate, based on constraints, optimal treatment plans tailored for various parameters (e.g., monetary value amount generated, patient outcome, risk, etc.). The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of the information (e.g., characteristics, medical diagnosis codes, etc.) pertaining to medical conditions of the people who used the treatment apparatus 70 to perform treatment plans, the details (e.g., treatment protocol including exercises, amount of time to perform the exercises, instructions for the patient to follow, how often to perform the exercises, a schedule of exercises, parameters/configurations/settings of the treatment apparatus 70 throughout each step of the treatment plan, etc.) of the treatment plans performed by the people using the treatment apparatus 70, the results of the treatment plans performed by the people, a set of monetary value amounts associated with the treatment plans, a set of constraints (e.g., rules pertaining to billing codes associated with the set of treatment plans, laws, regulations, etc.), a set of billing procedures (e.g., rules pertaining to billing codes, order, timing and constraints) associated with treatment plan instructions, a set of parameters (e.g., a fee to be paid to a medical professional, a payment plan for the patient to pay off an amount of money owed, a plan of reimbursement, an amount of revenue to be paid to an insurance provider, or some combination thereof, a treatment plan, a monetary value amount generated, a risk, etc.), insurance regimens, etc.

The one or more machine learning models 13 may be trained to match patterns of characteristics of a patient with characteristics of other people in assigned to a particular cohort. The term "match" may refer to an exact match, a correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, the machine learning apparatus 70.

The one or more machine learning models 13 may be trained to match patterns of a first set of parameters (e.g., treatment plans for patients having a medical condition, a set of monetary value amounts associated with the treatment plans, patient outcome, and/or a set of constraints) with a second set of parameters associated with an optimal treatment plan. The one or more machine learning models 13 may be trained to receive the first set of parameters as input, map the characteristics to the second set of parameters associated with the optimal treatment plan, and select the optimal treatment plan a treatment plan. The one or more machine learning models 13 may also be trained to control, based on the treatment plan, the machine learning apparatus 70.

The one or more machine learning models 13 may be trained to match patterns of a first set of parameters (e.g., information pertaining to a medical condition, treatment plans for patients having a medical condition, a set of monetary value amounts associated with the treatment plans, patient outcomes, instructions for the patient to follow in a treatment plan, a set of billing procedures associated with the instructions, and/or a set of constraints) with a second set of parameters associated with a billing sequence and/or optimal treatment plan. The one or more machine learning models 13 may be trained to receive the first set of parameters as input, map or otherwise associate or algorithmically associate the first set of parameters to the second set of parameters associated with the billing sequence and/or optimal treatment plan, and select the billing sequence and/or optimal treatment plan for the patient. In some embodiments, one or more optimal treatment plans may be selected to be provided to a computing device of the medical professional and/or the patient. The one or more machine learning models 13 may also be trained to control, based on the treatment plan, the machine learning apparatus 70.

Different machine learning models 13 may be trained to recommend different treatment plans tailored for different parameters. For example, one machine learning model may be trained to recommend treatment plans for a maximum monetary value amount generated, while another machine learning model may be trained to recommend treatment plans based on patient outcome, or based on any combination of monetary value amount and patient outcome, or based on those and/or additional goals. Also, different machine learning models 13 may be trained to recommend different billing sequences tailored for different parameters. For example, one machine learning model may be trained to recommend billing sequences for a maximum fee to be paid to a medical professional, while another machine learning model may be trained to recommend billing sequences based on a plan of reimbursement.

Using training data that includes training inputs and corresponding target outputs, the one or more machine learning models 13 may refer to model artifacts created by the training engine 9. The training engine 9 may find patterns in the training data wherein such patterns map the training input to the target output and generate the machine learning models 13 that capture these patterns. In some embodiments, the artificial intelligence engine 11, the database, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

In some embodiments, the output device 54 may present a user interface that may present a recommended treatment plan, billing sequence, or the like to the patient. The user interface may include one or more graphical elements that enable the user to select which treatment plan to perform. Responsive to receiving a selection of a graphical element (e.g., "Start" button) associated with a treatment plan via the input device 54, the patient interface 50 may communicate a control signal to the controller 72 of the treatment apparatus 70, wherein the control signal causes the treatment apparatus 70 to begin execution of the selected treatment plan. As described below, the control signal may control, based on the selected treatment plan, the treatment apparatus 70 by causing actuation of the actuator 78 (e.g., cause a motor to drive rotation of pedals of the treatment apparatus at a certain speed), causing measurements to be obtained via the sensor 76, or the like. The patient interface 50 may communicate, via a local communication interface 68, the control signal to the treatment apparatus 70.

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spinwheel, a smart-mirror, a treadmill, a vibratory apparatus, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, a velocity and/or an acceleration. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone. In some embodiments, the ambulation sensor 82 may be integrated within an article of clothing, such as a shoe, a belt, and/or pants.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, or a technician, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the assistant. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate treatment plans, billing sequences, and/or excluded treatment plans for patients and generate the display screens including those treatment plans, billing sequences, and/or excluded treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as an assistant remotely from any conventional office infrastructure. Such remote work may be performed, for example, where the assistant interface 94 takes the form of a computer and/or telephone. This remote work functionality may allow for work-from-home arrangements that may include part time and/or flexible work hours for an assistant.

Figure 2:
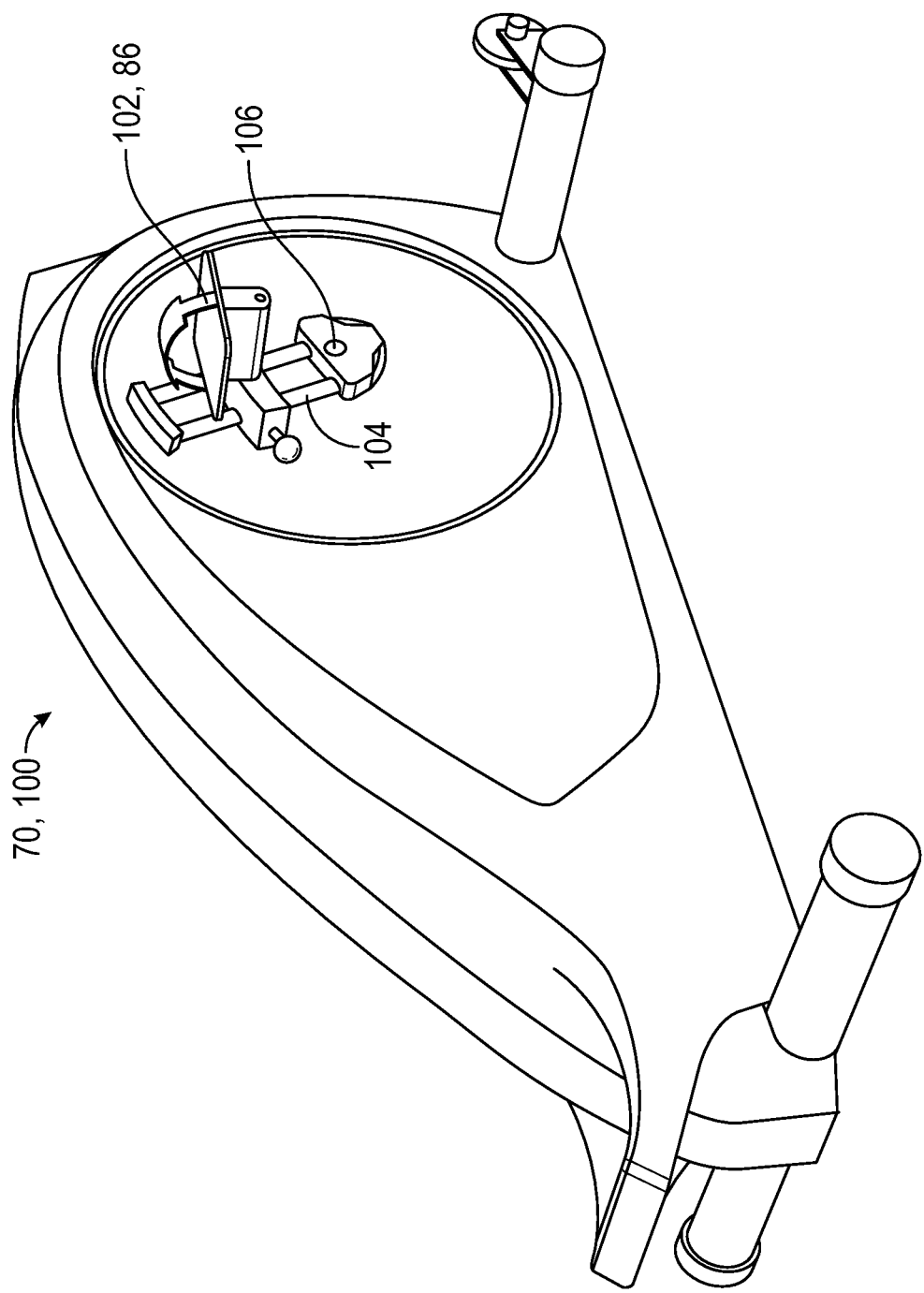
FIG. 2 shows a perspective view of an embodiment of a treatment apparatus according to the present disclosure.
Figure 3:
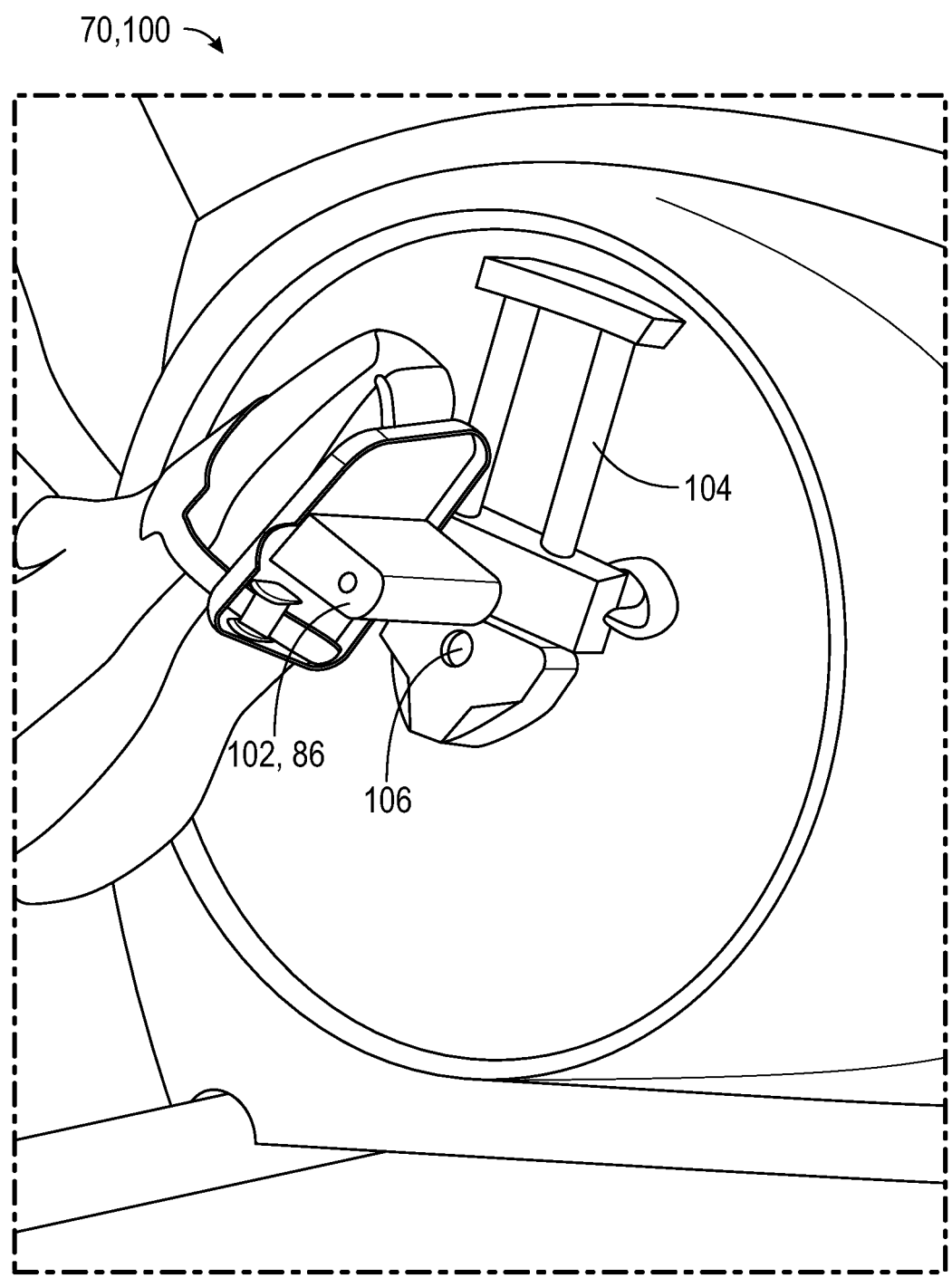
FIG. 3 shows a perspective view of a pedal of the treatment apparatus of FIG. 2 according to the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one or more of the pedals 102 for measuring an amount of force applied by the patient on the pedal 102. The pressure sensor 86 may communicate wirelessly to the treatment apparatus 70 and/or to the patient interface 50.

Figure 4:
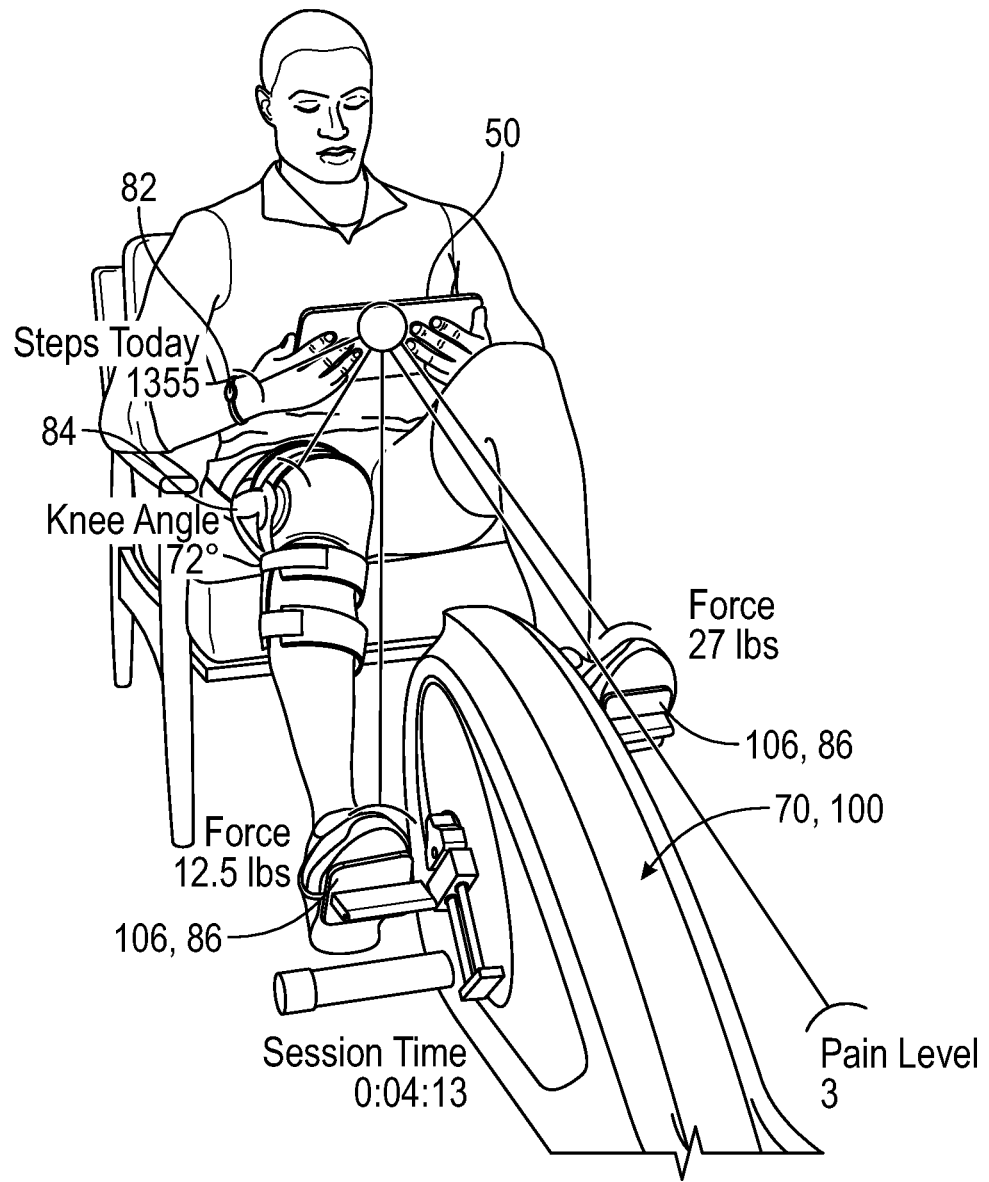
FIG. 4 shows a perspective view of a person using the treatment apparatus of FIG. 2 according to the present disclosure.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

Figure 5:
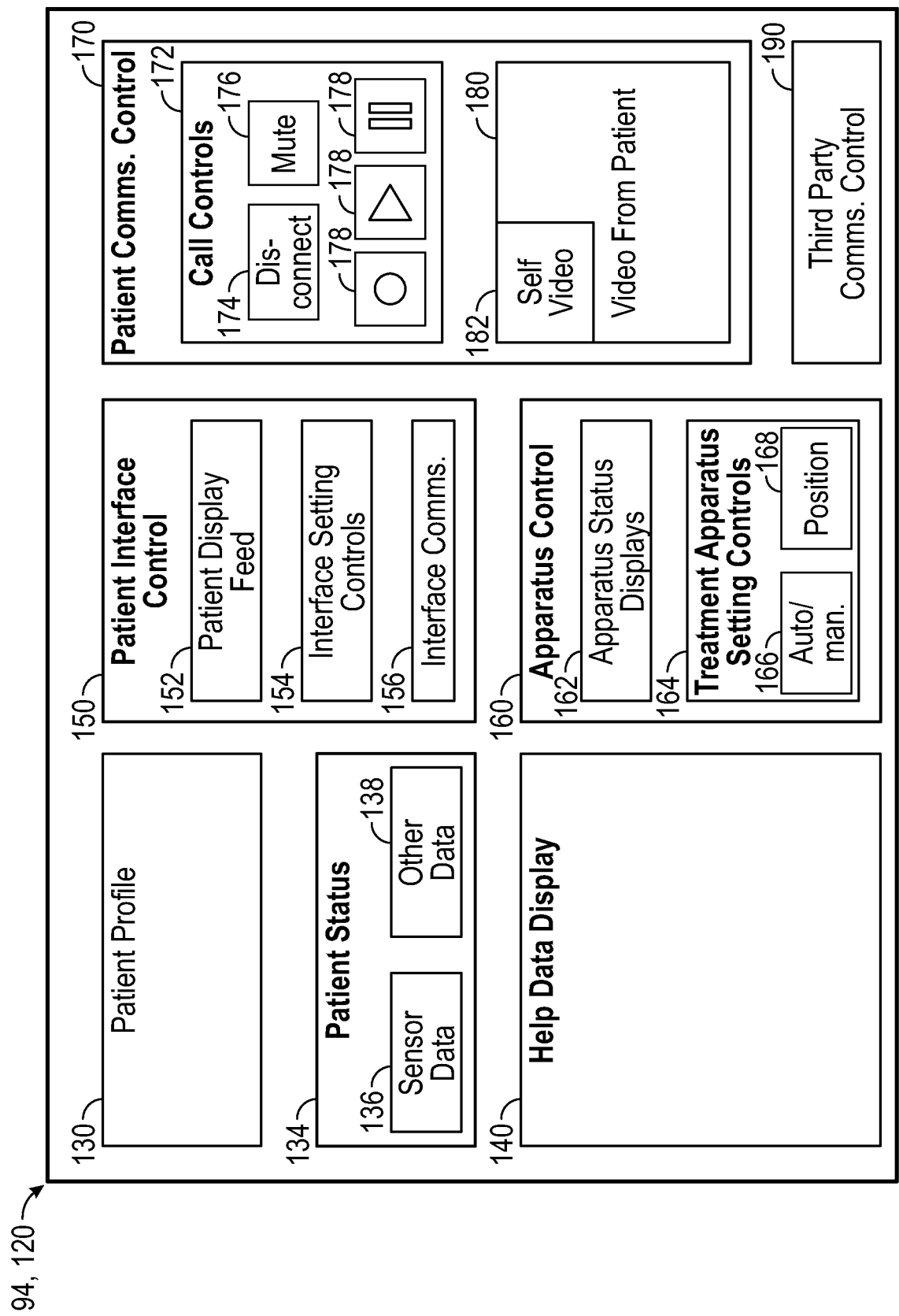
FIG. 5 shows an example embodiment of an overview display of an assistant interface according to the present disclosure.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the assistant's need for that information. For example, a medical professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to an assistant who is a medical professional, such as a doctor or physical therapist. For example, a medical professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans and/or excluded treatment plans may be presented in the patient profile display 130 to the assistant. The one or more recommended treatment plans and/or excluded treatment plans may be generated by the artificial intelligence engine 11 of the server 30 and received from the server 30 in real-time during, inter alia, a telemedicine or telehealth session. An example of presenting the one or more recommended treatment plans and/or ruled-out treatment plans is described below with reference to FIG. 7.

In some embodiments, one or more treatment plans and/or billing sequences associated with the treatment plans may be presented in the patient profile display 130 to the assistant. The one or more treatment plans and/or billing sequences associated with the treatment plans may be generated by the artificial intelligence engine 11 of the server 30 and received from the server 30 in real-time during, inter alia, a telehealth session. An example of presenting the one or more treatment plans and/or billing sequences associated with the treatment plans is described below with reference to FIG. 9.

In some embodiments, one or more treatment plans and associated monetary value amounts generated, patient outcomes, and risks associated with the treatment plans may be presented in the patient profile display 130 to the assistant. The one or more treatment plans and associated monetary value amounts generated, patient outcomes, and risks associated with the treatment plans may be generated by the artificial intelligence engine 11 of the server 30 and received from the server 30 in real-time during, inter alia, a telehealth session. An example of presenting the one or more treatment plans and associated monetary value amounts generated, patient outcomes, and risks associated with the treatment plans is described below with reference to FIG. 12.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant. for example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98*b*. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99*b*. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99 for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the assistant interface 94 and/or by another device or devices, such as a telephone system, or a videoconferencing system used by the assistant while the assistant uses the assistant interface 94. Alternatively or additionally, the audio and/or audiovisual communications may include communications with a third party. For example, the system 10 may enable the assistant to initiate a 3-way conversation regarding use of a particular piece of hardware or software, with the patient and a subject matter expert, such as a medical professional or a specialist. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily silence an audio or audiovisual signal from the assistant interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the assistant using the assistant interface. The self-video display 182 may be presented as a picture-in-picture format, within a section of the video feed display 180, as shown in FIG. 5. Alternatively or additionally, the self-video display 182 may be presented separately and/or independently from the video feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a medical professional or a specialist. The third party communications control 190 may include conference calling capability for the third party to simultaneously communicate with both the assistant via the assistant interface 94, and with the patient via the patient interface 50. For example, the system 10 may provide for the assistant to initiate a 3-way conversation with the patient and the third party.

Figure 6:
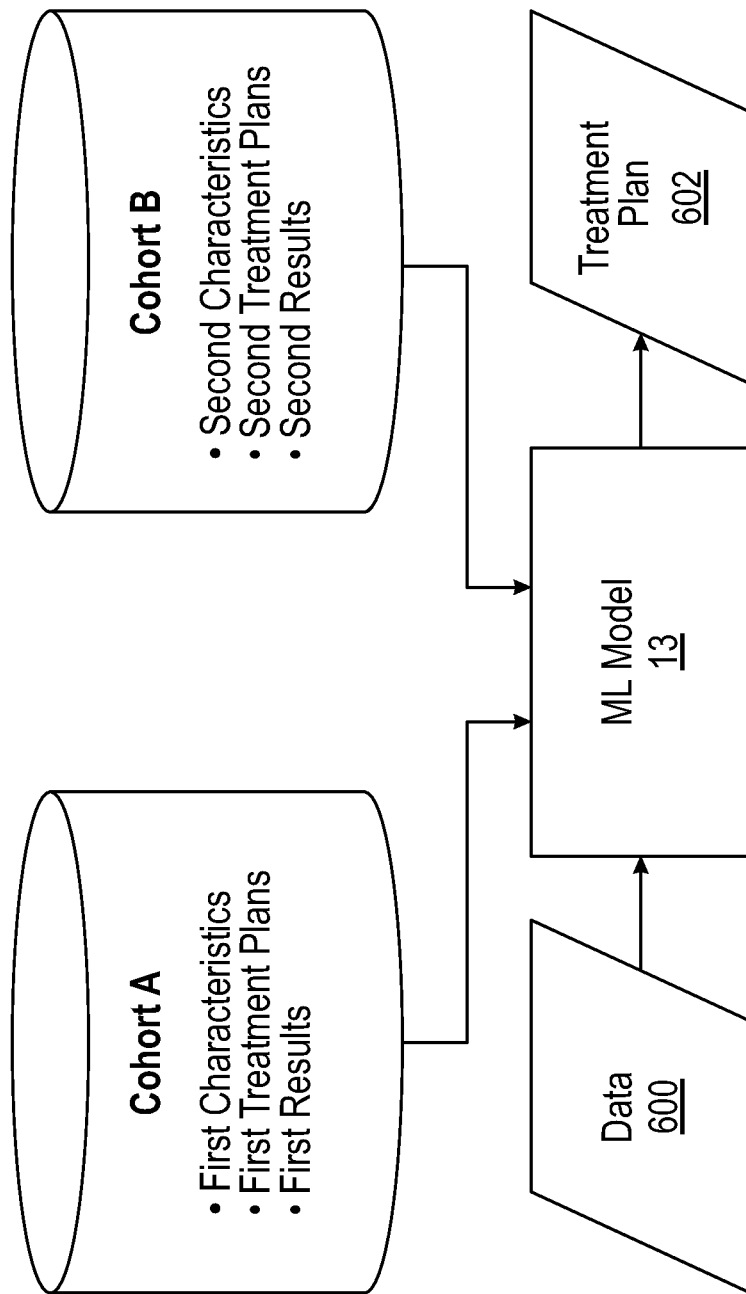
FIG. 6 shows an example block diagram of training a machine learning model to output, based on data pertaining to the patient, a treatment plan for the patient according to the present disclosure.

FIG. 6 shows an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment apparatus 70 for 30 minutes 5 times a week for 3 weeks, wherein values for the properties, configurations, and/or settings of the treatment apparatus 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan 602. In some embodiments, the machine learning model 13 may be trained to output one or more excluded treatment plans that should not be performed by the new patient.

Figure 7:
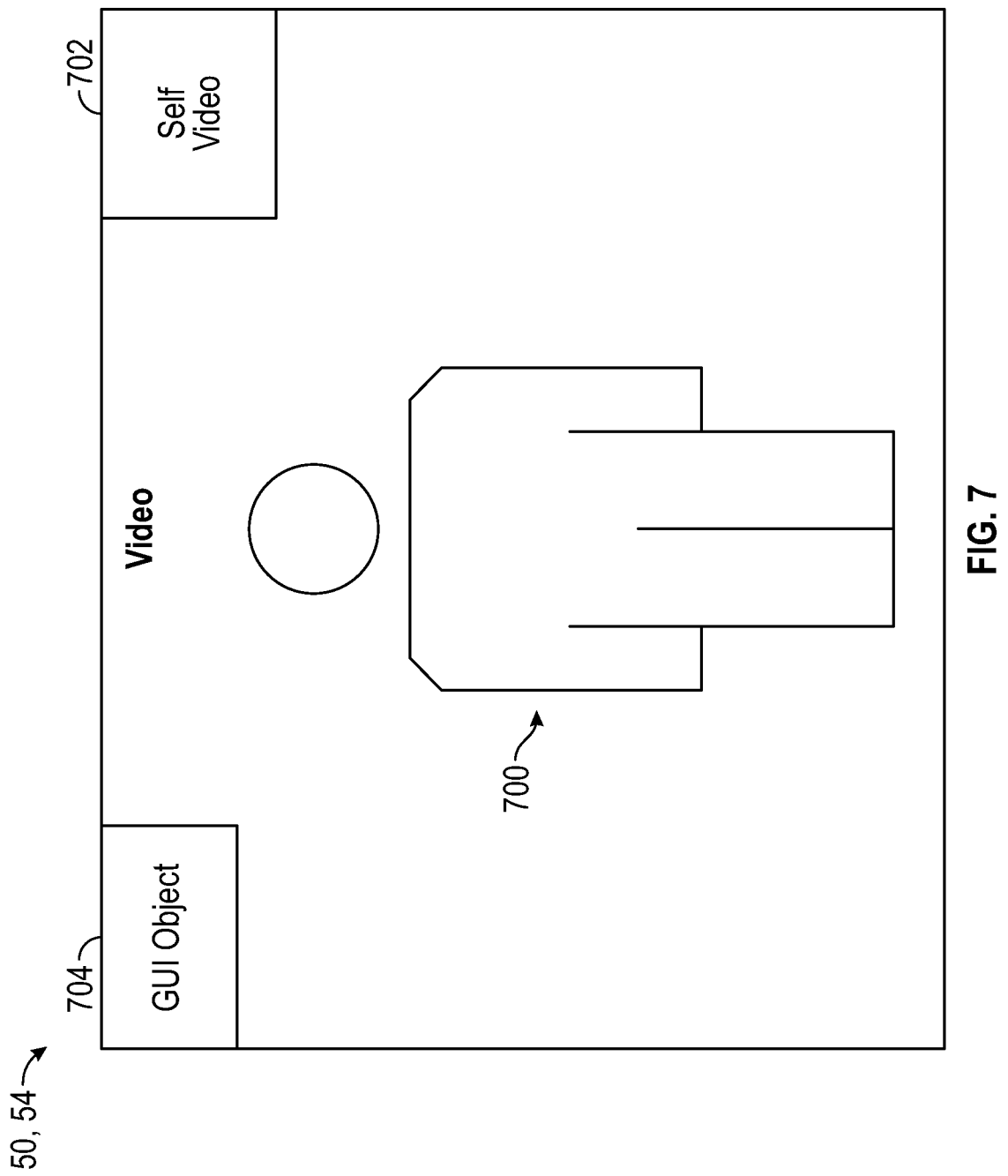
FIG. 7 shows an embodiment of an overview display of the patient interface presenting a virtual avatar guiding the patient through an exercise session according to the present disclosure.

FIG. 7 shows an embodiment of an overview display of the patient interface 50 presenting a virtual avatar 700 guiding the patient through an exercise session according to the present disclosure. The virtual avatar 700 may be presented on the output device 54 (e.g., display screen) of the patient interface 50. As depicted, the virtual avatar 700 may represent a person. In some embodiments, the person may be an actual individual, e.g., the medical professional, a professional athlete, the patient, a relative, a friend, a sibling, a celebrity, etc.; in other embodiments, the person may be fictional or constructed, e.g., a superhero, or the like. As discussed further herein, the virtual avatar may be any person, object, building, animal, being, alien, robot, or the like. For example, children may connect more strongly with animal animations to guide them through their exercise sessions. The virtual avatar 700 may be selected by the patient and/or the medical professional from a library of virtual avatars stored on a database at the server 30. In some embodiments, the virtual avatar may be able to be uploaded into the database or for private use by the patient and/or the medical professional. For example, the library of virtual avatars may be stored at the system data store 42 and/or the patient data store 44. Once the virtual avatar 700 has been selected for the patient, an identifier of the virtual avatar 700 may be associated with an identifier of the patient in the system data store 42 and/or the patient data store 44.

The virtual avatar 700 may perform one or more exercises specified in an exercise session of a treatment plan for the patient. As used throughout this disclosure, and for the avoidance of doubt, "exercises" may include, e.g., rehabilitation movements, high intensity interval training, strength training, range of motion training, or any body or physical movement capable of being performed on a treatment device specified in the treatment plan (including modifications or amendments or emendations thereto) or reasonably substituted for with a different treatment device. For example, one exercise may involve pedaling a stationary bicycle, and the virtual avatar 700 may be animated as pedaling the bicycle in a desired manner for the patient. In some embodiments, the virtual avatar 700 may include an actual video of a person performing the exercise session. Thus, the virtual avatar 700 may be generated by the server 30 and/or include audio, video, audiovisual and/or multimedia data of a real person performing the exercise session. In some embodiments, the virtual avatar 700 may represent a medical professional, such as a physical therapist, a coach, a trainer, etc.

In some embodiments, the virtual avatar 700 may be controlled by one or more machine learning models 13 of the artificial intelligence engine 11. For example, the one or more machine learning models 13 may be trained based on historical data and real-time or near-time data. The data used to train the machine learning models 13 may include previous feedback received from users (e.g., pain levels), characteristics of the patients at various points in their treatment plans (e.g., heartrate, blood pressure, temperature, perspiration rate, etc.), sensor measurements (e.g., pressure on pedals, range of motion, speed of the motor of the treatment apparatus 70, etc.) received as the patients performed their treatment plans, and/or the results achieved by the patients after certain operations are performed (e.g., initiating a telemedicine session with a multimedia feed of the medical professional, replacing the virtual avatar 700 with the multimedia feed of the medical professional, emoting certain auditory statements, presenting certain visuals on the output device 54, changing a parameter of the exercise session (e.g., reducing an amount of resistance provided by the treatment apparatus 70), etc.).

The output device 54 also presents a self-video section 702 that presents video of the patient obtained from a camera of the patient interface 50. The self-video may be used by the patient to verify whether they are using proper form, cadence, consistency or any other observable or measurable quality or quantity while performing an exercise session. While the patient performs the exercise session, the video obtained from the camera of the patient interface 50 may be transmitted to the assistant interface 94 for presentation. A medical professional may view the assistant interface 94 presenting the video of the patient and determine whether to intervene by speaking to the patient via their patient interface 50 and/or to replace the virtual avatar 700 with a multimedia feed from the assistant interface 94.

The output device 54 also presents a graphical user interface (GUI) object 704. The GUI object 704 may be an element that enables the user to provide feedback to the server 30. For example, the GUI object 704 may present a scale of values representing a level of pain the patient is currently experiencing, and the GUI object 704 may enable a patient to select a value representing their level of pain. The selection may cause a message to be transmitted to the server 30. In some embodiments, as described further herein, the message, including the level of pain, may pertain to a trigger event. The server 30 may determine whether the level of pain experienced by the patient exceeds a certain threshold severity level. If the level of pain exceeds the certain threshold severity level, then the server 30 may pause the virtual avatar 700 and/or replace the virtual avatar 700 with an audio, visual, audio-visual or multimedia feed from the computing device of a medical professional.

Figure 8:
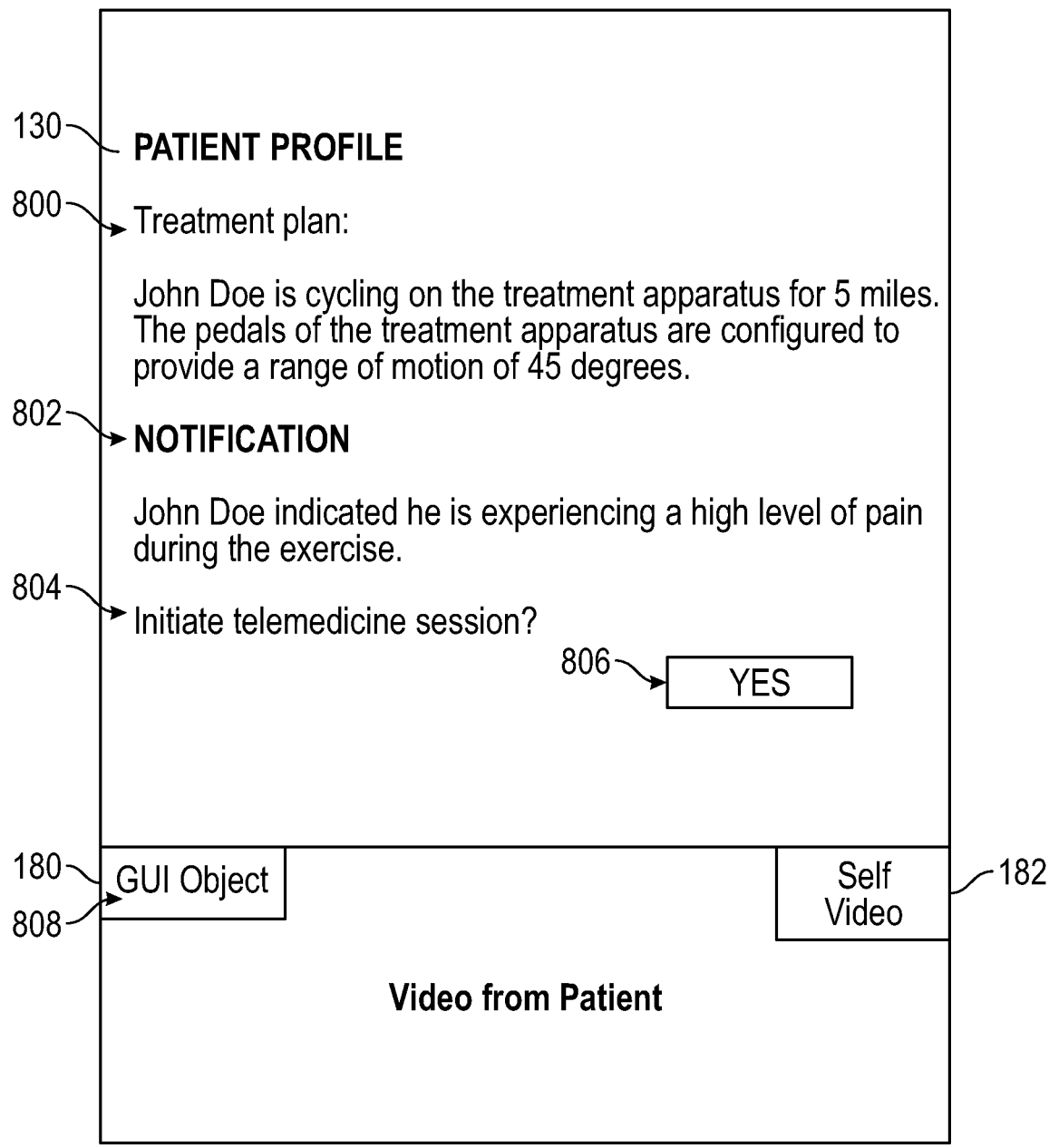
FIG. 8 shows an embodiment of the overview display of the assistant interface receiving a notification pertaining to the patient and enabling the assistant to initiate a telemedicine session in real-time according to the present disclosure.

FIG. 8 shows an embodiment of the overview display 120 of the assistant interface 94 receiving a notification pertaining to the patient and enabling the assistant (e.g., medical professional) to initiate a telemedicine session in real-time according to the present disclosure. As depicted, the overview display 120 includes a section for the patient profile 130. The patient profile 130 presents information pertaining to the treatment plan being performed by the patient "John Doe." The treatment plan 800 indicates that "John Doe is cycling on the treatment apparatus for 5 miles. The pedals of the treatment apparatus are configured to provide a range of motion of 45 degrees." The overview display 120 also includes a notification 802 that is received due to a trigger event. The notification presents "John Doe indicated he is experiencing a high level of pain during the exercise." The overview display 120 also includes a prompt 804 for a medical professional using the assistant interface 94. The prompt asks, "Initiate telemedicine session?" The overview display 120 includes a graphical element (e.g., button) 806 that is configured to enable the medical professional to use an wired or wireless input peripheral (e.g., touchscreen, mouse, keyboard, microphone, etc.) to select to initiate the telemedicine session. Although the above example details the overview display 120 of the assistant interface 94 presenting information in the form of text, an alternate or additional way of presenting that information can be in the form of graphs, charts, or the like.

The assistant (e.g., medical professional) using the assistant interface 94 (e.g., computing device) during the telemedicine session may be presented in the self-video 182 in a portion of the overview display 120 (e.g., user interface presented on a display screen 24 of the assistant interface 94). The assistant interface 94 may also present, in the same portion of the overview display 120 as the self-video, a video (e.g., self-video 182) from the patient in the video feed display 180. Further, the video feed display 180 may also include a graphical user interface (GUI) object 808 (e.g., a button) that enables the medical professional to share, in real-time or near real-time during the telemedicine session, a treatment plan with the patient on the patient interface 50, to control an operational parameter of the treatment apparatus 70, or the like.

Figure 9:
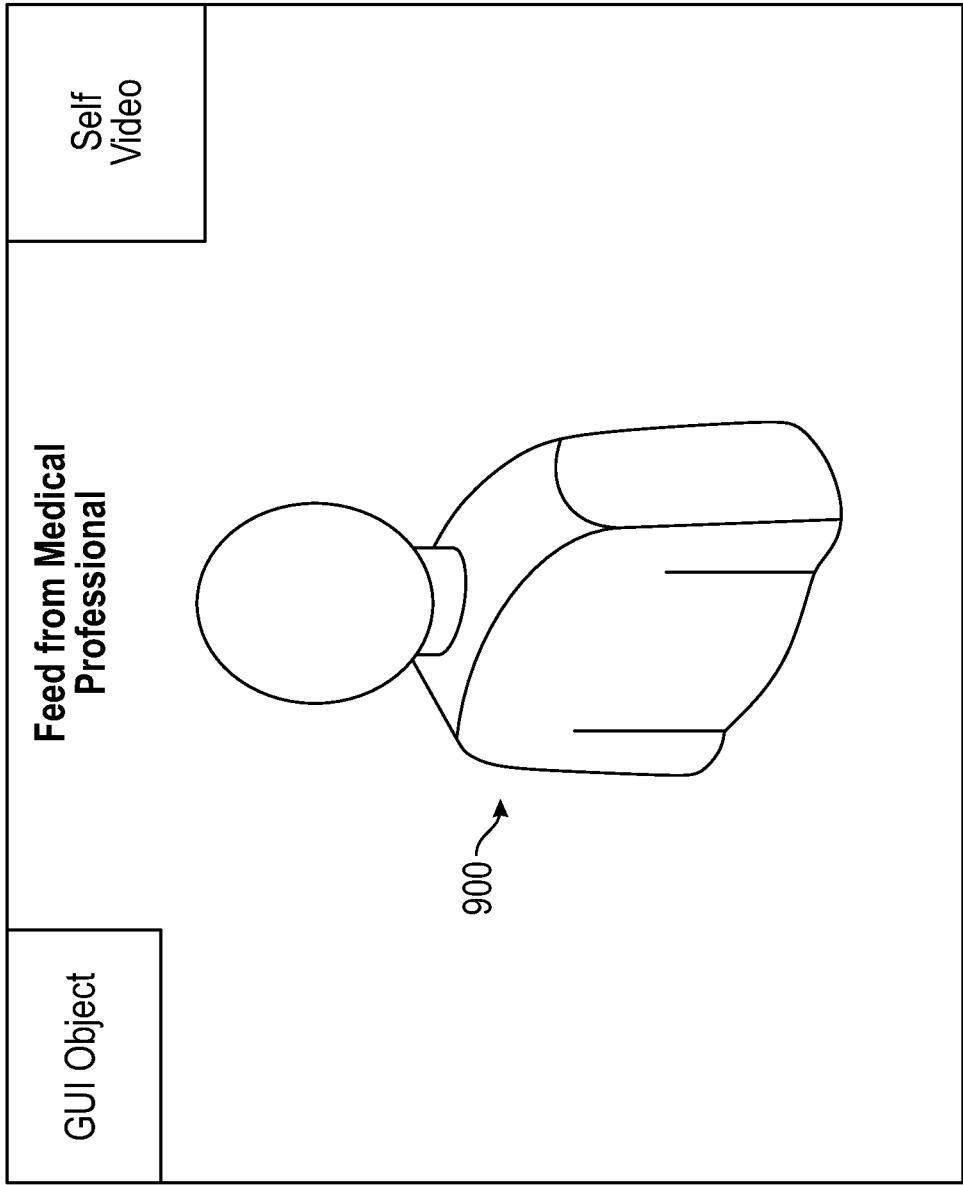
FIG. 9 shows an embodiment of the overview display of the patient interface presenting, in real-time during a telemedicine session, a feed of the medical professional that replaced the virtual avatar according to the present disclosure.

FIG. 9 shows an embodiment of an overview display presenting by the output device 54 of the patient interface 50. The output device 54 presents, in real-time during a telemedicine session, a feed 900 (e.g., multimedia preferably including audio, video, or both) of the medical professional that replaced the virtual avatar according to the present disclosure. In some embodiments, the virtual avatar may remain presented on the patient interface 50, but in a paused state, and the feed may preferably by limited to only audio when the medical professional speaks to the patient. In some embodiments, as depicted, the feed 900 may replace the virtual avatar. The feed may enable the medical professional and the patient to engage in a telemedicine session where the medical professional talks to the patient and inquires about their pain level, their characteristics (e.g., heartrate, perspiration rate, etc.), and/or one or more sensor measurements (e.g., pressure on pedals, range of motion, etc.).

It should be understood that the medical professional may be viewing, monitoring, treating, diagnosing, etc. numerous patients on the assistant interface 94 at the same time. For example, as discussed further below, each patient may be presented in a respective portion of the user interface of the assistant interface 94. Each respective portion may present a variety of information pertaining to the respective patient. For example, each portion may present a feed of the patient performing the exercise session using the treatment apparatus, characteristics of the patient, the treatment plan for the patient, sensor measurements, and the like. The user interface of the assistant interface 94 may be configured to enable the medical professional to select one or more patients to cause the virtual avatar guiding the one or more patients through an exercise to be paused and/or replaced in real-time or near real-time.

Upon completion of the telemedicine session between the patient interface 50 and the assistant interface 94, the feed from the computing device of the medical professional may be replaced with the virtual avatar on the patient interface 50. The virtual avatar may continue guiding the patient through the exercise session wherever and/or whenever the exercise session was paused due to the initiation of the trigger event. The assistant interface 94 may resume viewing the feed of the patient performing the exercise session and/or information pertaining to the patient.

Figure 10:
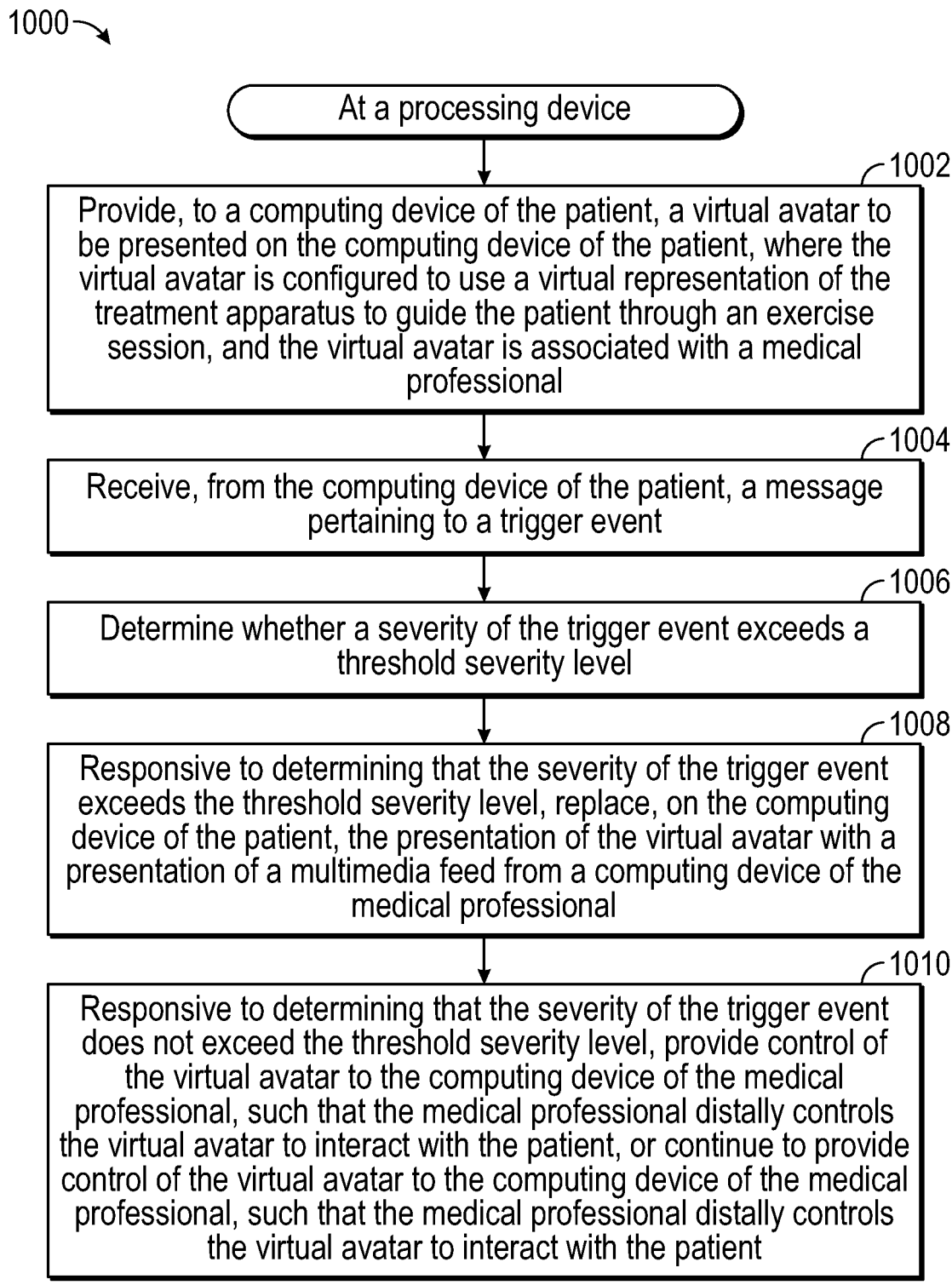
FIG. 10 shows an example embodiment of a method for replacing, based on a trigger event occurring, a virtual avatar with a feed of a medical professional according to the present disclosure.

FIG. 10 shows an example embodiment of a method 1000 for replacing, based on a trigger event occurring, a virtual avatar with a feed of a medical professional according to the present disclosure. The method 1000 is performed by processing logic that may include hardware (circuitry, dedicated logic, etc.), software (such as is run on a general-purpose computer system or a dedicated machine), or a combination of both. The method 1000 and/or each of its individual functions, routines, other methods, scripts, subroutines, or operations may be performed by one or more processors of a computing device (e.g., any component of FIG. 1, such as server 30 executing the artificial intelligence engine 11). In certain implementations, the method 1000 may be performed by a single processing thread. Alternatively, the method 1000 may be performed by two or more processing threads, each thread implementing one or more individual functions or routines; or other methods, scripts, subroutines, or operations of the methods.

For simplicity of explanation, the method 1000 is depicted and described as a series of operations. However, operations in accordance with this disclosure can occur in various orders and/or concurrently, and/or with other operations not presented and described herein. For example, the operations depicted in the method 1000 may occur in combination with any other operation of any other method disclosed herein. Furthermore, not all illustrated operations may be required to implement the method 1000 in accordance with the disclosed subject matter. In addition, those skilled in the art will understand and appreciate that the method 1000 could alternatively be represented as a series of interrelated states via a state diagram, a directed graph, a deterministic finite state automaton, a non-deterministic finite state automaton, a Markov diagram, or event diagrams.

At 1002, the processing device may provide, to a computing device (e.g., patient interface 50) of the patient, a virtual avatar to be presented on the computing device of the patient. The virtual avatar may be configured to use a virtual representation of the treatment apparatus 70 to guide the patient through an exercise session. The virtual avatar may be configured to use audio, video, haptic feedback, or some combination thereof, to guide the patient through the exercise session. The audio, video, haptic feedback, or some combination thereof, may be provided by the computing device of the patient. In some embodiments, the processing device may determine, based on a treatment plan for a patient, the exercise session to be performed. The treatment apparatus 70 may be configured to be used by the patient performing the exercise session.

In some embodiments, prior to providing the virtual avatar, the processing device may transmit, to the computing device of the patient, a notification to initiate the exercise session. The notification may include a push notification, a text message, a phone call, an email, or some combination thereof. The notification may be transmitted based on a schedule specified in the treatment plan. The schedule may include dates and times to perform exercise sessions, durations for performing the exercise sessions, exercises to perform during the exercise sessions, configurations of parts (e.g., pedals, seat, etc.) of the treatment apparatus 70, and the like. The processing device may receive, from the computing device of the patient, a selection to initiate the exercise session for using the treatment apparatus 70. The processing device may transmit, to the treatment apparatus 70, a control signal to cause the treatment apparatus 70 to initiate the exercise session. Responsive to transmitting the control signal, the processing device may provide the virtual avatar to the computing device of the patient.

The virtual avatar may be associated with a medical professional, such as the medical professional that prescribed or generated the treatment plan for the patient to perform. In some embodiments, the treatment plan may be wholly or partially designed generated by the medical professional. In some embodiments, the treatment plan may be wholly or partially generated by the artificial intelligence engine 11, and the medical professional may review the treatment plan and/or modify the treatment plan before it is transmitted to the patient to be performed.

The virtual avatar may represent a proxy medical professional and may be a person, being, thing, software or electronic bot, object, etc. that guides one or more patients through a treatment plan. The virtual avatar may guide numerous patients through treatment plans at various stages of their rehabilitation, prehabilitation, recovery, etc. It should be noted that at any time the virtual avatar may be replaced by a feed (e.g., live audio, audiovisual, etc.) of the medical professional, wherein the feed is transmitted, either directly to or indirectly through the server 30, from the assistant interface 94 to the patient interface 50. The feed may be a stream of data packets (e.g., audio, video, or both) obtained via a camera and/or microphone associated with the assistant interface 94 in real-time or near real-time. The feed may be presented on the user interface 54 of the patient interface 50.

In some embodiments, the virtual avatar may be initially selected by the medical professional. The virtual avatar may be a file stored in a virtual avatar library, and the medical professional may select the virtual avatar from the virtual avatar library. For example, the virtual avatar may be a life-like representation of a person (e.g., male, female, non-binary, or any other gender with which the person identifies). In some embodiments, the virtual avatar may be a life-like or virtual representation of an animal (e.g., tiger, lion, unicorn, rabbit, etc.), which may be more enjoyable and more motivational to younger people (e.g., kids). In some embodiments, the virtual avatar may be a life-like or virtual representation of a robot, alien, etc.

In some embodiments, the medical professional may design their own virtual avatar. For example, the medical professional may be provided with a user interface on their assistant interface 94, and the user interface may provide user interface elements that enable configuration of a virtual avatar. The medical professional may use the user interface to generate a virtual avatar that looks like their own self or any suitable person.

In some embodiments, the virtual avatar may be selected by the patient. In some embodiments, the selected virtual avatar may be associated with the patient (e.g., via an identifier of the patient and an identifier of the virtual avatar) and stored in a database. For example, some patients may have a preference for certain virtual avatars over other virtual avatars. In some embodiments, different virtual avatars may guide patients through the same or different treatment plan. With respect to any treatment plan referenced herein, different aspects, portions or configurations of the treatment plan may further be guided by more than one virtual or physical avatar, wherein each such avatar is associated with a particular aspect, portion or configuration of the treatment plan, and every other avatar, to the extent application is associated with a disjoint aspect, portion or configuration of the treatment plan. In other embodiments, more than one avatar, physical and/or virtual, may be present at the same time but performing different functions within the particular aspect, portion or configuration of the treatment plan. In group therapy sessions, numerous patients may be performing the same treatment plan, and each patient may have their own patient interface 50 that concurrently presents the same or a different virtual avatar or avatars guiding the patient through the treatment plan.

As the patients perform the treatment plan, the medical professional may be able to view the numerous patients in different tiles on the user interface of the assistant interface 94. The term "tiles" may refer to squares that each include a feed from the respective patient interfaces 50 of the patient as the patient performs the treatment plan, a feed of the characteristics of the patient (e.g., heartrate, blood pressure, temperature, etc.), a feed of measurements (e.g., pressure exerted on the pedals, range of motion determined by the goniometer, number of steps, speed of the motor of the treatment apparatus 70, etc.), or some combination thereof. As such, using the disclosed embodiments, the medical professional may be enabled to manage, monitor, and/or treat numerous patients at a time. Computing resources may be saved by having one medical professional treatment numerous patients at the same time because just the assistant interface 94 is used to view, treat, manage, monitor, etc. the numerous patients as they perform the treatment plan.

At 1004, the processing device may receive, from the computing device of the patient, a message pertaining to a trigger event. In some embodiments, the message may include data pertaining to a pain level of the patient, a characteristic of the patient, a measurement of a sensor, or some combination thereof. The trigger event may refer to any event associated with the data pertaining to the pain level of the patient, the characteristic of the patient (e.g., heartrate, blood pressure, temperature, perspiration rate, etc.), the measurement of the sensor (e.g., pressure, range of motion, speed, etc.), or some combination thereof.

In some instances, the virtual avatar may guide the patient through the treatment plan as a prerecorded animation, and the medical professional may not be actively engaged in a telemedicine session with the patient as they perform the treatment plan. In some embodiments, when the trigger event occurs, a notification may be transmitted to the computing device of the medical professional, where such device alerts the medical professional about the notification. The medical professional may use a wired or wireless input peripheral (e.g., touchscreen, mouse, keyboard, microphone) to select the notification and to initiate a telemedicine session with the computing device of the patient. Such a technique may minimize or otherwise optimize the use and/or cost and/or risk profile of one or more computing resources, such as network resources (e.g., bandwidth), by initiating the telemedicine session only when the notification is selected and not throughout the entirety of the treatment plan. In other embodiments, the computing device of the medical professional and the computing device of the patient and the computing device of the medical professional may be continuously or continually engaged in a telemedicine session as the one or more patients perform the treatment plan. The trigger event may enable the medical professional to intervene and/or replace the virtual avatar, pause the virtual avatar, or both. In some embodiments, while the patients are performing the treatment plan, the medical professional may selectively choose one or more of the patients to cause the virtual avatar on those one or more patients' computing devices to be replaced, paused, etc. Such a technique may enable the medical professional to intervene for some of the patients, but not for all of the patients, as they perform the treatment plan. For example, the medical professional may select patients not hitting target thresholds (e.g., pressure, range of motion, speed, etc.) in the treatment plan, select patients indicating they are experiencing a threshold level of pain, or the like.

In some embodiments, the virtual avatar may be controlled, in real-time or near real-time, by one or more machine learning models trained to receive input, including sensor data (e.g., pressure measurements from the pedals, range of motion measurements from a goniometer, speed data, etc.), characteristics of the patient (e.g., perspiration rate, heartrate, blood pressure, temperature, arterial blood gas and/or oxygenation levels or percentages etc.), real-time feedback from the patient or other patients (e.g., indication of pain level), or some combination thereof. The one or more machine learning models may produce an output that controls the virtual avatar. For example, the output may control the virtual avatar such that the way the virtual avatar performs a particular exercise (e.g., pedals faster or slower on a treatment apparatus 70) is modified, to say encouraging statements (e.g., "You got this," "Keep it up," etc.), etc. The modifications may be based on training data of other patients, where such training data indicates the modifications result in a desired patient performance and/or result for the other patients, or an increase in the probability of achieving the desired patient performance or result. For example, the training data may indicate that providing certain audio and/or video when certain sensor data is detected may lead to the patient exerting more force on the pedal, thereby strengthening their leg muscles according to the treatment plan.

At 1006, the processing device may determine whether a severity level of the trigger event exceeds a threshold severity level. The severity threshold level may be any suitable amount, value, indicator, etc. For example, in one embodiment, the threshold severity level may be a certain level of pain the patient is in. At any time during an exercise session, the patient may use any input peripheral of the patient interface 50 to express their level of pain. For example, the patient may touch a button on the touchscreen of the patient interface 50 and the button may indicate the patient is experiencing a pain level of 8 in a scale from 1 to 10, where 1 is the least amount of pain and 10 is the most amount of pain. In this example, the threshold severity level may be a pain level of 5. Accordingly, the level of pain (8) the patient is experiencing exceeds the threshold severity level (5). In some embodiments, the threshold severity level may relate to the amount of force the patient is exerting on the pedals, a range of motion the patient is able to achieve during pedaling, a speed the patient is able to achieve, a duration of a range of motion and/or speed the patient is able to achieve, or the like. For example, the threshold severity level may be configured based on the patient pedaling at a certain range of motion for a certain period of time, and if the patient fails to achieve the certain range of motion in the certain period of time, or variations thereof of such goals, during an exercise session, then the threshold severity level may be exceeded.

At 1008, responsive to determining the severity level of the trigger event exceeds the threshold severity level, the processing device may replace, on the computing device of the patient, the presentation of the virtual avatar with a presentation of a multimedia feed from a computing device (e.g., assistant interface 94) of the medical professional. In some embodiments, replacing the virtual avatar with the multimedia feed may initiate a telemedicine session between the patient and the medical professional. The processing device may receive, from the computing device of the patient or the medical professional, a second message indicating the telemedicine session is complete, and the processing device may replace, on the computing device of the patient, the presentation of the multimedia feed with the presentation of the virtual avatar. The virtual avatar may be configured to continue to guide the patient through the exercise session to completion. That is, the exercise session and/or the virtual avatar may be paused at a certain timestamp when the multimedia feed of the medical professional replaces the virtual avatar, and the exercise session and/or the virtual avatar may initiate playback at the certain timestamp when the telemedicine session is completed.

In some embodiments, at 1010, responsive to determining that the severity level of the trigger event does not exceed the threshold severity level, the processing device may provide control of the virtual avatar to the computing device of the medical professional, such that the medical professional distally controls the virtual avatar to interact with the patient. In some embodiments, responsive to determining that the severity level of the trigger event does not exceed the threshold severity level, the processing device may continue to provide control of the virtual avatar to the computing device of the medical professional, such that the medical professional distally controls the virtual avatar to interact with the patient.

In some embodiments, the processing device may determine, based on a second treatment plan for a second patient, the exercise session to be performed, where the performance by the second patient uses a second treatment apparatus. The processing device may present, on a second computing device (e.g., patient interface 50) of the second patient, the virtual avatar configured to guide the patient to use the treatment apparatus through the exercise session. In some embodiments, while the presentation of the virtual avatar is replaced on the computing device of the patient with the presentation of the multimedia feed from the computing device of the medical professional, the virtual avatar may remain presented on the second computing device of the second patient. In some embodiments, while the presentation of the virtual avatar is replaced on the computing device of the patient with the presentation of the multimedia feed from the computing device of the medical professional, the virtual avatar may be replaced on the second computing device of the second patient with the multimedia feed from the computing device of the medical professional.

Figure 11:
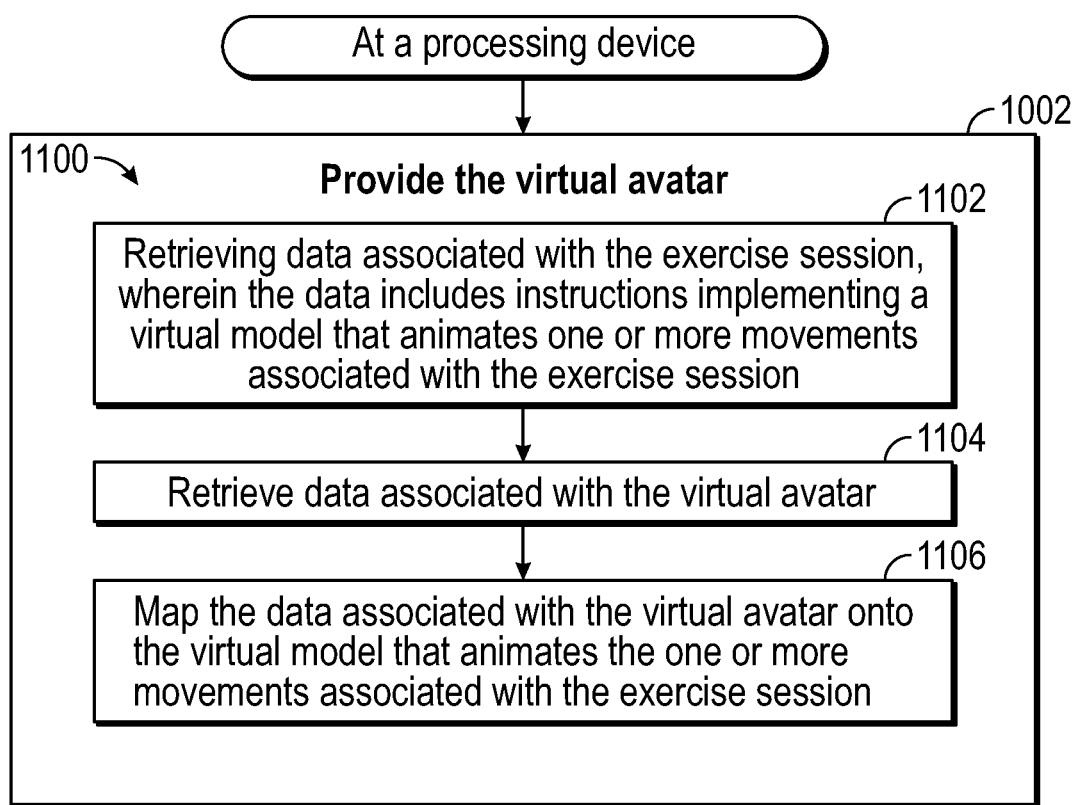
FIG. 11 shows an example embodiment of a method for providing a virtual avatar according to the present disclosure.

FIG. 11 shows an example embodiment of a method for providing a virtual avatar according to the present disclosure. Method 1100 includes operations performed by processors of a computing device (e.g., any component of FIG. 1, such as server 30 executing the artificial intelligence engine 11). In some embodiments, one or more operations of the method 1100 are implemented in computer instructions stored on a memory device and executed by a processing device. The method 1100 may be performed in the same or a similar manner as described above in regard to method 1000. The operations of the method 1100 may be performed in some combination with any of the operations of any of the methods described herein. The method 1100 may include further operations associated with 1002 in method 1000 related to providing the virtual avatar to the computing device of the patient.

At 1102, the processing device may retrieve data associated with the exercise session. The data may include instructions implementing a virtual model that animates one or more movements associated with the exercise session. The virtual model may be two-dimensional, three-dimensional, or n-dimensional (in terms of animations or projections onto a 3-D virtual environment or a 2-D layout). In some embodiments, the virtual model may be a mesh model animation, contour animation, virtual human animation, skeletal animation, etc. For example, the virtual model may be a surface representation (referred to as the mesh) used to draw a character (e.g., medical professional), and a hierarchical set of interconnected parts. The virtual model may use a virtual armature to animate (e.g., pose and key frame) the mesh. As used herein, an armature may refer to a kinematic chain used in computer animation to simulate the motions of virtual human or animal characters (e.g., virtual avatars). Various types of virtual armatures may be used, such as keyframing (stop-motion) armatures and real-time (puppeteering) armatures.

At 1104, the processing device may retrieve data associated with the virtual avatar. The data associated with the virtual avatar may include which virtual avatar is selected by the patient and/or the medical professional, wherein such selection is made to guide the patient through the exercise session. In some embodiments, the data associated with the virtual avatar may include an identifier associated with the virtual avatar. The identifier may be used to retrieve the data associated with the virtual avatar from a database. For example, the patient may have selected a superhero to be their virtual avatar. Accordingly, data pertaining to the particular superhero (e.g., gender, costume, appearance, etc.) may be retrieved from the database.

At 1106, the processing device may map the data associated with the virtual avatar onto the virtual model that animates the one or more movements associated with the exercise session. For example, the appearance and shape of the virtual avatar may be mapped onto the mesh of the virtual model (e.g., face to a head portion of the mesh) and manipulated and/or animated according to instructions related to the exercise session and/or the virtual avatar. In some embodiments, the virtual avatar may perform one or more exercises using the treatment apparatus 70. The performance of the exercises by the virtual avatar may be animated and/or presented on a display screen of the computing device of the patient to guide the patient through the exercise session. As disclosed herein, at any time, the virtual avatar may be replaced and/or paused to enable presentation of a multimedia feed of a medical professional.

Figure 12:
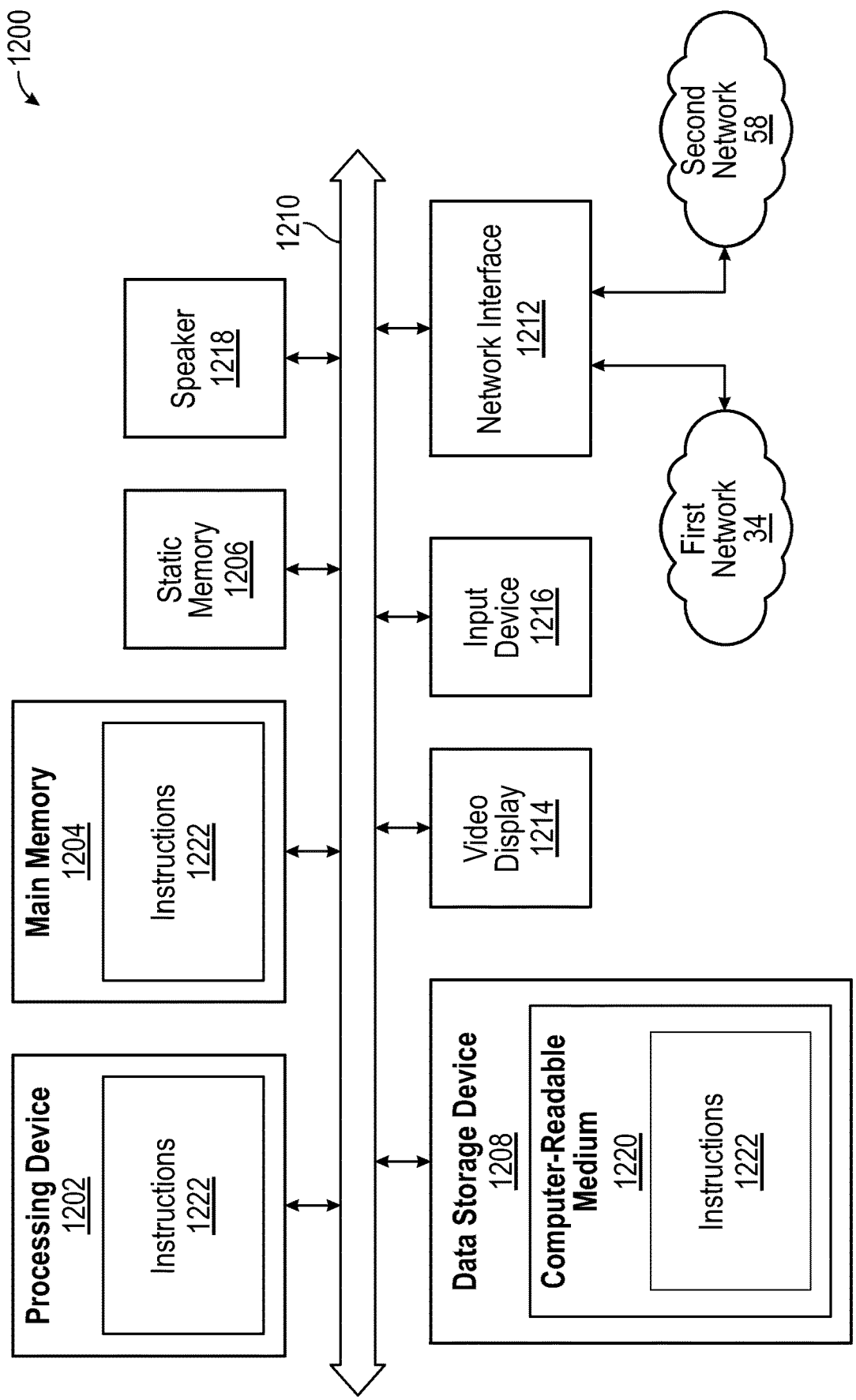
FIG. 12 shows an example computer system according to the present disclosure.

FIG. 12 shows an example computer system 1200 which can perform any one or more of the methods described herein, in accordance with one or more aspects of the present disclosure. In one example, computer system 1200 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1200 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1200 includes a processing device 1202, a main memory 1204 (e.g., read-only memory (ROM), flash memory, solid state drives (SSDs), dynamic random access memory (DRAM) such as synchronous DRAM (SDRAM)), a static memory 1206 (e.g., flash memory, solid state drives (SSDs), static random access memory (SRAM)), and a data storage device 1208, which communicate with each other via a bus 1210.

Processing device 1202 represents one or more general-purpose processing devices such as a microprocessor, central processing unit, or the like. More particularly, the processing device 1202 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1200 may further include a network interface device 1212. The computer system 1200 also may include a video display 1214 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1216 (e.g., a keyboard and/or a mouse or a gaming-like control), and one or more speakers 1218 (e.g., a speaker). In one illustrative example, the video display 1214 and the input device(s) 1216 may be combined into a single component or device (e.g., an LCD touch screen).

The data storage device 1216 may include a computer-readable medium 1220 on which the instructions 1222 embodying any one or more of the methods, operations, or functions described herein is stored. The instructions 1222 may also reside, completely or at least partially, within the main memory 1204 and/or within the processing device 1202 during execution thereof by the computer system 1200. As such, the main memory 1204 and the processing device 1202 also constitute computer-readable media. The instructions 1222 may further be transmitted or received over a network via the network interface device 1212.

While the computer-readable storage medium 1220 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A computer-implemented system, comprising:
a treatment apparatus configured to be manipulated by a patient while performing an exercise session;
a patient interface configured to receive a virtual avatar, wherein the patient interface comprises an output device configured to present the virtual avatar, wherein the virtual avatar uses a virtual representation of the treatment apparatus to guide the patient through an exercise session, and wherein the virtual avatar is associated with a medical professional; and
a server computing device configured to:
provide the virtual avatar of the patient to the patient interface,
receive, from the patient interface, a message pertaining to a trigger event, and wherein the message comprises a severity level of the trigger event,
determine whether a severity level of the trigger event exceeds a threshold severity level, and
responsive to determining that the severity level of the trigger event exceeds the threshold severity level, replace on the patient interface the presentation of the virtual avatar with a presentation of a multimedia feed from a computing device of the medical professional.

Clause 2. The computer-implemented system of clause 1, wherein the server computing device is further to:
responsive to determining that the severity level of the trigger event does not exceed the threshold severity level:
provide control of the virtual avatar to the computing device of the medical professional, such that the medical professional distally controls the virtual avatar to interact with the patient, or
continue to provide control of the virtual avatar to the computing device of the medical professional, such that the medical professional distally controls the virtual avatar to interact with the patient.

Clause 3. The computer-implemented system of clause 1, wherein the virtual avatar is controlled, in real-time or near real-time, by one or more machine learning models trained to:
receive input comprising sensor data, characteristics of the patient, real-time feedback from the patient or other patients, or some combination thereof, and
produce an output that controls the virtual avatar.

Clause 4. The computer-implemented system of clause 1, wherein providing the virtual avatar further comprises:
retrieving data associated with the exercise session, wherein the data comprises instructions implementing a virtual model that animates one or more movements associated with the exercise session;
retrieving data associated with the virtual avatar; and
mapping the data associated with the virtual avatar onto the virtual model that animates the one or more movements associated with the exercise session.

Clause 5. The computer-implemented system of clause 1, wherein prior to providing the virtual avatar, the server computing device is further to:
transmit, to the patient interface, a notification to initiate the exercise session, wherein the notification is transmitted based on a schedule specified in the treatment plan;
receive, from the patient interface, a selection to initiate the exercise session for using the treatment apparatus;
transmit, to the treatment apparatus, a control signal to cause the treatment apparatus to initiate the exercise session; and
responsive to transmitting the control signal, provide the virtual avatar to the patient interface.

Clause 6. The computer-implemented system of clause 5, wherein the notification comprises a push notification, a text message, a phone call, an email, or some combination thereof.

Clause 7. The computer-implemented system of clause 1, wherein the server computing device is further to:
determine, based on a second treatment plan for a second patient, the exercise session to be performed, wherein the performance by the second patient uses a second treatment apparatus;
present, on a second patient interface of the second patient, the virtual avatar configured to guide the patient to use the treatment apparatus through the exercise session, wherein:
while the presentation of the virtual avatar is replaced on the patient interface with the presentation of the multimedia feed from the computing device of the medical professional, the virtual avatar remains presented on the second patient interface, or
while the presentation of the virtual avatar is replaced on the patient interface with the presentation of the multimedia feed from the computing device of the medical professional, the virtual avatar is replaced on the second patient interface with the multimedia feed from the computing device of the medical professional.

Clause 8. The method of clause 1, wherein the server computing device is further to:
receive, from the patient interface, a selection of the virtual avatar from a library of virtual avatars; and
store the virtual avatar associated with the patient in a database.

Clause 9. The method of clause 1, wherein the virtual avatar is configured to use audio, video, haptic feedback, or some combination thereof to guide the patient through the exercise session.

Clause 10. A method comprising:
providing, to a computing device of the patient, a virtual avatar to be presented on the computing device of the patient, wherein the virtual avatar is configured to use a virtual representation of the treatment apparatus to guide the patient through an exercise session, and the virtual avatar is associated with a medical professional;
receiving, from the computing device of the patient, a message pertaining to a trigger event;
determining whether a severity level of the trigger event exceeds a threshold severity level; and
responsive to determining that the severity level of the trigger event exceeds the threshold severity level, replacing, on the computing device of the patient, the presentation of the virtual avatar with a presentation of a multimedia feed from a computing device of the medical professional.

Clause 11. The method of clause 10, further comprising:
responsive to determining that the severity level of the trigger event does not exceed the threshold severity level:
providing control of the virtual avatar to the computing device of the medical professional, such that the medical professional distally controls the virtual avatar to interact with the patient, or
continuing to provide control of the virtual avatar to the computing device of the medical professional, such that the medical professional distally controls the virtual avatar to interact with the patient.

Clause 12. The method of clause 10, wherein the virtual avatar is controlled, in real-time or near real-time, by one or more machine learning models trained to:
receive input comprising sensor data, characteristics of the patient, real-time feedback from the patient or other patients, or some combination thereof, and
produce an output that controls the virtual avatar.

Clause 13. The method of clause 10, wherein providing the virtual avatar further comprises:
retrieving data associated with the exercise session, wherein the data comprises instructions implementing a virtual model that animates one or more movements associated with the exercise session;
retrieving data associated with the virtual avatar; and
mapping the data associated with the virtual avatar onto the virtual model that animates the one or more movements associated with the exercise session.

Clause 14. The method of clause 10, wherein prior to providing the virtual avatar, the method further comprises:
transmitting, to the computing device of the patient, a notification to initiate the exercise session, wherein the notification is transmitted based on a schedule specified in the treatment plan;
receiving, from the computing device of the patient, a selection to initiate the exercise session for using the treatment apparatus;

transmitting, to the treatment apparatus, a control signal to cause the treatment apparatus to initiate the exercise session; and responsive to transmitting the control signal, providing the virtual avatar to the computing device of the patient.

Clause 15. The method of clause 14, wherein the notification comprises a push notification, a text message, a phone call, an email, or some combination thereof.

Clause 16. The method of clause 10, further comprising:

determining, based on a second treatment plan fora second patient, the exercise session to be performed, wherein the performance by the second patient uses a second treatment apparatus;

presenting, on a second computing device of the second patient, the virtual avatar configured to guide the patient to use the treatment apparatus through the exercise session, wherein:

while the presentation of the virtual avatar is replaced on the computing device of the patient with the presentation of the multimedia feed from the computing device of the medical professional, the virtual avatar remains presented on the second computing device, or while the presentation of the virtual avatar is replaced on the computing device of the patient with the presentation of the multimedia feed from the computing device of the medical professional, the virtual avatar is replaced on the second computing device with the multimedia feed from the computing device of the medical professional.

Clause 17. The method of clause 10, further comprising:

receiving, from the computing device of the patient, a selection of the virtual avatar from a library of virtual avatars; and storing the virtual avatar associated with the patient in a database.

Clause 18. The method of clause 10, wherein the virtual avatar is configured to use audio, video, haptic feedback, or some combination thereof to guide the patient through the exercise session.

Clause 19. The method of clause 10, wherein the message comprises data pertaining to a pain level of the patient, a characteristic of the patient, a measurement of a sensor, or some combination thereof.

Clause 20. The method of clause 10, wherein replacing the virtual avatar with the multimedia feed initiates a telemedicine session between the patient and the medical professional, and the method further comprises:

receiving, from the computing device of the patient or the medical professional, a second message indicating the telemedicine session is complete; and replacing, on the computing device of the patient, presentation of the multimedia feed with the presentation of the virtual avatar, wherein the virtual avatar is configured to continue to guide the patient through the exercise session to completion.

Clause 21. The method of clause 10, further comprising determining, based on a treatment plan for a patient, the exercise session to be performed, wherein the treatment apparatus is configured to be used by the patient performing the exercise session.

Clause 22. A non-transitory, tangible computer-readable medium storing instructions that, when executed, cause a processing device to:

provide, to a computing device of a patient, a virtual avatar to be presented on the computing device of the patient, wherein the virtual avatar is configured to use a virtual representation of a treatment apparatus to guide the patient through an exercise session, and the virtual avatar is associated with a medical professional;

receive, from the computing device of the patient, a message pertaining to a trigger event;

determine whether a severity level of the trigger event exceeds a threshold severity level; and responsive to determining that the severity level of the trigger event exceeds the threshold severity level, replace, on the computing device of the patient, the presentation of the virtual avatar with a presentation of a multimedia feed from a computing device of the medical professional.

Clause 23. The computer-readable medium of clause 22, wherein, responsive to determining that the severity level of the trigger event does not exceed the threshold severity level, the processing device is further to:

provide control of the virtual avatar to the computing device of the medical professional, such that the medical professional distally controls the virtual avatar to interact with the patient, or continue to provide control of the virtual avatar to the computing device of the medical professional, such that the medical professional distally controls the virtual avatar to interact with the patient.

Clause 24. The computer-readable medium of clause 22, wherein the virtual avatar is controlled, in real-time or near real-time, by one or more machine learning models trained to:

receive input comprising sensor data, characteristics of the patient, real-time feedback from the patient or other patients, or some combination thereof, and produce an output that controls the virtual avatar.

Clause 25. The computer-readable medium of clause 22, wherein providing the virtual avatar further comprises:

retrieving data associated with the exercise session, wherein the data comprises instructions implementing a virtual model that animates one or more movements associated with the exercise session;

retrieving data associated with the virtual avatar; and mapping the data associated with the virtual avatar onto the virtual model that animates the one or more movements associated with the exercise session.

Clause 26. The computer-readable medium of clause 22, wherein prior to providing the virtual avatar, the processing device is further to:

transmit, to the computing device of the patient, a notification to initiate the exercise session, wherein the notification is transmitted based on a schedule specified in the treatment plan;

receive, from the computing device of the patient, a selection to initiate the exercise session for using the treatment apparatus;

transmit, to the treatment apparatus, a control signal to cause the treatment apparatus to initiate the exercise session; and responsive to transmitting the control signal, provide the virtual avatar to the computing device of the patient.

Clause 27. A system comprising:

a memory device storing instructions;

a processing device communicatively coupled to the memory device, the processing device executes the instructions to:

provide, to a computing device of a patient, a virtual avatar to be presented on the computing device of the patient, wherein the virtual avatar is configured to use a virtual representation of a treatment apparatus to guide the patient through an exercise session, and the virtual avatar is associated with a medical professional;

receive, from the computing device of the patient, a message pertaining to a trigger event;

determine whether a severity level of the trigger event exceeds a threshold severity level; and responsive to determining that the severity level of the trigger event exceeds the threshold severity level, replace, on the computing device of the patient, the presentation of the virtual avatar with a presentation of a multimedia feed from a computing device of the medical professional.

Clause 28. The system of clause 27, wherein, responsive to determining that the severity level of the trigger event does not exceed the threshold severity level, the processing device is further to:

provide control of the virtual avatar to the computing device of the medical professional, such that the medical professional distally controls the virtual avatar to interact with the patient, or continue to provide control of the virtual avatar to the computing device of the medical professional, such that the medical professional distally controls the virtual avatar to interact with the patient.

Clause 29. The system of clause 27, wherein the processing device is further to:

retrieve data associated with the exercise session, wherein the data comprises instructions implementing a virtual model that animates one or more movements associated with the exercise session;

retrieve data associated with the virtual avatar; and map the data associated with the virtual avatar onto the virtual model that animates the one or more movements associated with the exercise session.

Clause 30. The system of clause 27, wherein prior to providing the virtual avatar, the processing device is further to:

transmit, to the computing device of the patient, a notification to initiate the exercise session, wherein the notification is transmitted based on a schedule specified in the treatment plan;

receive, from the computing device of the patient, a selection to initiate the exercise session for using the treatment apparatus;

transmit, to the treatment apparatus, a control signal to cause the treatment apparatus to initiate the exercise session; and responsive to transmitting the control signal, provide the virtual avatar to the computing device of the patient.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

What is claimed is:

1. A computer-implemented system, comprising:

a treatment apparatus configured to be manipulated by a patient while performing an exercise session;

a patient interface configured to receive a virtual avatar, wherein the patient interface comprises an output device configured to present the virtual avatar, wherein the virtual avatar uses a virtual representation of the treatment apparatus to guide the patient through an exercise session, and wherein the virtual avatar is associated with a medical professional; and a server computing device configured to:

provide the virtual avatar of the patient to the patient interface, receive, from the patient interface, a message pertaining to a trigger event, and wherein the message comprises a severity level of the trigger event, determine whether a severity level of the trigger event exceeds a threshold severity level, and responsive to determining that the severity level of the trigger event exceeds the threshold severity level, replace on the patient interface the presentation of the virtual avatar with a presentation of a multimedia feed from a computing device of the medical professional.

2. The computer-implemented system of claim 1, wherein the server computing device is further to:

responsive to determining that the severity level of the trigger event does not exceed the threshold severity level:

provide control of the virtual avatar to the computing device of the medical professional, such that the medical professional distally controls the virtual avatar to interact with the patient, or continue to provide control of the virtual avatar to the computing device of the medical professional, such that the medical professional distally controls the virtual avatar to interact with the patient.

3. The computer-implemented system of claim 1, wherein the virtual avatar is controlled, in real-time or near real-time, by one or more machine learning models trained to:

receive input comprising sensor data, characteristics of the patient, real-time feedback from the patient or other patients, or some combination thereof, and produce an output that controls the virtual avatar.

4. The computer-implemented system of claim 1, wherein providing the virtual avatar further comprises:

retrieving data associated with the exercise session, wherein the data comprises instructions implementing a virtual model that animates one or more movements associated with the exercise session;

retrieving data associated with the virtual avatar; and mapping the data associated with the virtual avatar onto the virtual model that animates the one or more movements associated with the exercise session.

5. The computer-implemented system of claim 1, wherein prior to providing the virtual avatar, the server computing device is further to:

transmit, to the patient interface, a notification to initiate the exercise session, wherein the notification is transmitted based on a schedule specified in the treatment plan;

receive, from the patient interface, a selection to initiate the exercise session for using the treatment apparatus;

transmit, to the treatment apparatus, a control signal to cause the treatment apparatus to initiate the exercise session; and responsive to transmitting the control signal, provide the virtual avatar to the patient interface.

6. The computer-implemented system of claim 5, wherein the notification comprises a push notification, a text message, a phone call, an email, or some combination thereof.

7. The computer-implemented system of claim 1, wherein the server computing device is further to:

determine, based on a second treatment plan for a second patient, the exercise session to be performed, wherein the performance by the second patient uses a second treatment apparatus;

present, on a second patient interface of the second patient, the virtual avatar configured to guide the patient to use the treatment apparatus through the exercise session, wherein:

while the presentation of the virtual avatar is replaced on the patient interface with the presentation of the multimedia feed from the computing device of the medical professional, the virtual avatar remains presented on the second patient interface, or while the presentation of the virtual avatar is replaced on the patient interface with the presentation of the multimedia feed from the computing device of the medical professional, the virtual avatar is replaced on the second patient interface with the multimedia feed from the computing device of the medical professional.

8. The computer-implemented system of claim 1, wherein the server computing device is further to:

receive, from the patient interface, a selection of the virtual avatar from a library of virtual avatars; and store the virtual avatar associated with the patient in a database.

9. The computer-implemented system of claim 1, wherein the virtual avatar is configured to use audio, video, haptic feedback, or some combination thereof to guide the patient through the exercise session.

10. A method comprising:

providing, to a computing device of the patient, a virtual avatar to be presented on the computing device of the patient, wherein the virtual avatar is configured to use a virtual representation of the treatment apparatus to guide the patient through an exercise session, and the virtual avatar is associated with a medical professional;

receiving, from the computing device of the patient, a message pertaining to a trigger event;

determining whether a severity level of the trigger event exceeds a threshold severity level; and responsive to determining that the severity level of the trigger event exceeds the threshold severity level, replacing, on the computing device of the patient, the presentation of the virtual avatar with a presentation of a multimedia feed from a computing device of the medical professional.

11. The method of claim 10, further comprising:

responsive to determining that the severity level of the trigger event does not exceed the threshold severity level:

providing control of the virtual avatar to the computing device of the medical professional, such that the medical professional distally controls the virtual avatar to interact with the patient, or continuing to provide control of the virtual avatar to the computing device of the medical professional, such that the medical professional distally controls the virtual avatar to interact with the patient.

12. The method of claim 10, wherein the virtual avatar is controlled, in real-time or near real-time, by one or more machine learning models trained to:

receive input comprising sensor data, characteristics of the patient, real-time feedback from the patient or other patients, or some combination thereof, and produce an output that controls the virtual avatar.

13. The method of claim 10, wherein providing the virtual avatar further comprises:

retrieving data associated with the exercise session, wherein the data comprises instructions implementing a virtual model that animates one or more movements associated with the exercise session;

retrieving data associated with the virtual avatar; and mapping the data associated with the virtual avatar onto the virtual model that animates the one or more movements associated with the exercise session.

14. The method of claim 10, wherein prior to providing the virtual avatar, the method further comprises:

transmitting, to the computing device of the patient, a notification to initiate the exercise session, wherein the notification is transmitted based on a schedule specified in the treatment plan;

receiving, from the computing device of the patient, a selection to initiate the exercise session for using the treatment apparatus;

transmitting, to the treatment apparatus, a control signal to cause the treatment apparatus to initiate the exercise session; and responsive to transmitting the control signal, providing the virtual avatar to the computing device of the patient.

15. The method of claim 14, wherein the notification comprises a push notification, a text message, a phone call, an email, or some combination thereof.

16. The method of claim 10, further comprising:

determining, based on a second treatment plan for a second patient, the exercise session to be performed, wherein the performance by the second patient uses a second treatment apparatus;

presenting, on a second computing device of the second patient, the virtual avatar configured to guide the patient to use the treatment apparatus through the exercise session, wherein:

while the presentation of the virtual avatar is replaced on the computing device of the patient with the presentation of the multimedia feed from the computing device of the medical professional, the virtual avatar remains presented on the second computing device, or while the presentation of the virtual avatar is replaced on the computing device of the patient with the presentation of the multimedia feed from the computing device of the medical professional, the virtual avatar is replaced on the second computing device with the multimedia feed from the computing device of the medical professional.

17. The method of claim 10, further comprising:

receiving, from the computing device of the patient, a selection of the virtual avatar from a library of virtual avatars; and storing the virtual avatar associated with the patient in a database.

18. The method of claim 10, wherein the virtual avatar is configured to use audio, video, haptic feedback, or some combination thereof to guide the patient through the exercise session.

19. The method of claim 10, wherein the message comprises data pertaining to a pain level of the patient, a characteristic of the patient, a measurement of a sensor, or some combination thereof.

20. The method of claim 10, wherein replacing the virtual avatar with the multimedia feed initiates a telemedicine session between the patient and the medical professional, and the method further comprises:

receiving, from the computing device of the patient or the medical professional, a second message indicating the telemedicine session is complete; and replacing, on the computing device of the patient, presentation of the multimedia feed with the presentation of the virtual avatar, wherein the virtual avatar is configured to continue to guide the patient through the exercise session to completion.

21. The method of claim 10, further comprising determining, based on a treatment plan for a patient, the exercise session to be performed, wherein the treatment apparatus is configured to be used by the patient performing the exercise session.

22. A non-transitory, tangible computer-readable medium storing instructions that, when executed, cause a processing device to:

provide, to a computing device of a patient, a virtual avatar to be presented on the computing device of the patient, wherein the virtual avatar is configured to use a virtual representation of a treatment apparatus to guide the patient through an exercise session, and the virtual avatar is associated with a medical professional;

receive, from the computing device of the patient, a message pertaining to a trigger event;

determine whether a severity level of the trigger event exceeds a threshold severity level; and responsive to determining that the severity level of the trigger event exceeds the threshold severity level, replace, on the computing device of the patient, the presentation of the virtual avatar with a presentation of a multimedia feed from a computing device of the medical professional.

23. The computer-readable medium of claim 22, wherein, responsive to determining that the severity level of the trigger event does not exceed the threshold severity level, the processing device is further to:

provide control of the virtual avatar to the computing device of the medical professional, such that the medical professional distally controls the virtual avatar to interact with the patient, or continue to provide control of the virtual avatar to the computing device of the medical professional, such that the medical professional distally controls the virtual avatar to interact with the patient.

24. The computer-readable medium of claim 22, wherein the virtual avatar is controlled, in real-time or near real-time, by one or more machine learning models trained to:

receive input comprising sensor data, characteristics of the patient, real-time feedback from the patient or other patients, or some combination thereof, and produce an output that controls the virtual avatar.

25. The computer-readable medium of claim 22, wherein providing the virtual avatar further comprises:

retrieving data associated with the exercise session, wherein the data comprises instructions implementing a virtual model that animates one or more movements associated with the exercise session;

retrieving data associated with the virtual avatar; and mapping the data associated with the virtual avatar onto the virtual model that animates the one or more movements associated with the exercise session.

26. The computer-readable medium of claim 22, wherein prior to providing the virtual avatar, the processing device is further to:

transmit, to the computing device of the patient, a notification to initiate the exercise session, wherein the notification is transmitted based on a schedule specified in the treatment plan;

receive, from the computing device of the patient, a selection to initiate the exercise session for using the treatment apparatus;

transmit, to the treatment apparatus, a control signal to cause the treatment apparatus to initiate the exercise session; and responsive to transmitting the control signal, provide the virtual avatar to the computing device of the patient.

27. A system comprising:

a memory device storing instructions;

a processing device communicatively coupled to the memory device, the processing device executes the instructions to:

provide, to a computing device of a patient, a virtual avatar to be presented on the computing device of the patient, wherein the virtual avatar is configured to use a virtual representation of a treatment apparatus to guide the patient through an exercise session, and the virtual avatar is associated with a medical professional;

receive, from the computing device of the patient, a message pertaining to a trigger event;

determine whether a severity level of the trigger event exceeds a threshold severity level; and responsive to determining that the severity level of the trigger event exceeds the threshold severity level, replace, on the computing device of the patient, the presentation of the virtual avatar with a presentation of a multimedia feed from a computing device of the medical professional.

28. The system of claim 27, wherein, responsive to determining that the severity level of the trigger event does not exceed the threshold severity level, the processing device is further to:

provide control of the virtual avatar to the computing device of the medical professional, such that the medical professional distally controls the virtual avatar to interact with the patient, or continue to provide control of the virtual avatar to the computing device of the medical professional, such that the medical professional distally controls the virtual avatar to interact with the patient.

29. The system of claim 27, wherein the processing device is further to:

retrieve data associated with the exercise session, wherein the data comprises instructions implementing a virtual model that animates one or more movements associated with the exercise session;

retrieve data associated with the virtual avatar; and map the data associated with the virtual avatar onto the virtual model that animates the one or more movements associated with the exercise session.

30. The system of claim 27, wherein prior to providing the virtual avatar, the processing device is further to:

transmit, to the computing device of the patient, a notification to initiate the exercise session, wherein the notification is transmitted based on a schedule specified in the treatment plan;

receive, from the computing device of the patient, a selection to initiate the exercise session for using the treatment apparatus;

transmit, to the treatment apparatus, a control signal to cause the treatment apparatus to initiate the exercise session; and responsive to transmitting the control signal, provide the virtual avatar to the computing device of the patient.

* * * * *